United States Patent [19]

Kornbluth et al.

[11] Patent Number: 4,785,077
[45] Date of Patent: Nov. 15, 1988

[54] SUBSTANTIALLY PURE CYTOTOXICITY TRIGGERING FACTOR

[75] Inventors: Richard Kornbluth, San Diego; Thomas S. Edgington, La Jolla; Susan A. Gregory, San Diego, all of Calif.

[73] Assignee: Scripps Clinic and Research Foundation, La Jolla, Calif.

[21] Appl. No.: 859,604

[22] Filed: May 5, 1986

[51] Int. Cl.[4] .................. C07K 15/00; C12N 5/00
[52] U.S. Cl. ...................... 530/351; 530/350; 530/827; 435/68; 435/948; 435/240.31; 424/85.4; 424/85.1
[58] Field of Search .................. 530/350–351, 530/827; 435/68, 240, 241, 948

[56] References Cited

U.S. PATENT DOCUMENTS 4,383,985  5/1983  Bartorelli et al. .................. 424/1
4,725,669  2/1988  Essex et al. .................. 530/322

OTHER PUBLICATIONS

Chandmasekaran et al., *PNAS* 78(11) 1981, pp. 6953–6957.
Wood et al., *Virology* 105, 1980, pp. 148–158.
Kornbluth et al., Fed. Proc., vol. 44, 1985.
Gregory et al., *J. Immunol.*, 137:3231–3239 (1986).
Roberts et al., *J. Interferon Res.*, 2:519–532 (1982).
Stutman et al., *Lymphokines* 12:107–159 (1985).
Boraschi et al., *Lymphokines*, 9:71–108 (1984).
Immunology, Bach ed., John Wiley & Sons, New York (1982) p. 984.
Molecular Biology of the Cell, Alberts et al., Garland Publishing, Inc., New York (1983) p. 996.
Principles of Biochemistry, White et al., McGraw-Hill Book Co., New York (1978) p. 939.
Parker et al., *J. Immunol.*, 122:1572–1577 (1979).
Cellular Functions in Immunity and Inflammation, Oppenheim et al. eds., Elsevier/North-Holland, New York (1981) p. 169.
Immunopharmacology and the Regulation of Leukocyte Function, Webb, ed., Marcel Dekker, Inc., New YOrk (1982) pp. 143–158.
Krammer et al., *J. Immunol.*, 135:3258–3263 (1985).
Hammann et al., *Eur. J. Immunol.*, 15:18–24 (1985).
Esparza et al., *J. Exp. Med.*, 166:589–594 (1987).

*Primary Examiner*—Johnnie R. Brown
*Assistant Examiner*—Garnette D. Draper
*Attorney, Agent, or Firm*—Dressler, Goldsmith, Shore, Sutker & Milnamow, Ltd.

[57] ABSTRACT

A new, human proteinaceous lymphokine denominated cytotoxicity triggering factor (CTF) is disclosed as are methods of its preparation and use. Substantially pure CTF has an apparent $M_r$ of about 55 kd, is capable of inducing secretion of a tumor-killing factor containing tumor necrosis factor-alpha from primed monocytes, and is substantially free from pyrogen as well as interferon-gamma, interleukin-2 and direct cytotoxin.

20 Claims, 7 Drawing Sheets

Cytotoxicity (% Specific Release)

SUBSTANTIALLY PURE CYTOTOXICITY TRIGGERING FACTOR

DESCRIPTION

1. Technical Field

The present invention relates to T cell induction of peripheral blood mononuclear cell effector function, and particularly to a human proteinaceous lymphokine that acts on primed peripheral blood mononuclear cells such as monocytes to induce cytotoxicity against tumor cells.

2. Background

Cells of the monocyte/macrophage lineage possess diverse effector potential including antimicrobial function, mediation of cellular cytotoxicity, initiation of the coagulation and fibrinolytic protease pathways, synthesis of complement proteins and secretion of immunologically significant monokines such as interleukin-1 (IL-1) and tumor necrosis factor-alpha (TNF-A). These states of cellular activation and molecular products can be induced by appropriate signals. Cohn, (1978) *J. Immunol.* 121:813; North, (1981) *Lymphokines* 3:1; Adams et al. (1984) *Ann. Rev. Immunol.* 2:283; Edgington, et al., (1985) *Mononuclear Phagocytes*, 687–696; Vassalli et al. (1977) *J. Exp. Med.* 145:429; Littman et al. (1977) *J. Exp. Med.* 145:1344; and Dinarello (1984) *Rev. Infect. Dis.* 6:51.

These cellular functions are coupled to the immune response by selected T lymphocyte-mediated collaborative interactions of either contact- or lymphokine-mediated type. The responses are immunologically induced in the T cell that in turn instruct the expression of monocyte/macrophage effector functions that themselves are not antigen specific [Nathan et al. (1983), *J. Exp. Med.* 158:670; Gregory et al. (1985), *J. Clin. Invest.* 76:2440; Herrmann et al. (1985), *J. Exp. Med.* 162:1111; and Amento et al. (1985) *J. Immunol.* 134:350], but are nonetheless central to immunologic responses in vivo.

Studies of human and murine monocytes and macrophages have consistently demonstrated that cells of the mononuclear phagocyte system physiologically exist in a resting or latent state and do not normally express their potent capacities for tumor cell and pathogen destruction. Instead, a sequence of steps is required for macrophages, which mature from blood monocytes upon migration into the tissues, to express these highly developed responses in vivo or in vitro.

A set of one or more lymphokines, as well as certain unrelated agonists, has been implicated in monocyte/macrophage activation. This material is referred to as "macrophage-activating factor" (MAF), a component of the cellular immune effector response. Fidler, (1984) *Lymphokine Research* 3:51. With the recognition that interferon-gamma (IFN-G) has profound effects on monocytes and macrophages [Nathan et al., (1983) *J. Exp. Med.* 158:670; and Nathan et al., *J. Exp. Med.* 160:600], IFN-G proved to be the first molecularly defined T lymphocyte product identified as a MAF that is associated with the priming phase of a complex sequence of changes in the function of macrophages. IFN-G is also referred to herein as MAF-I. Pace et al., (1983) *J. Immunol.* 130:2011; Pace et al. (1983) *Proc. Natl. Acad. Sci. U.S.A.* 80:3782; Fischer et al., (1983) *J. Immunol.* 130:1220; Le et al., (1983) *J. Immunol.* 131:2821; Saklik et al., (1985) *Cancer Res.* 45:1940; and Svedersky et al. (1984) *J. Exp. Med.* 159:812.

It has been evident for some time that a sequence of signals must be provided to elicit the activated phenotype of monocytes and macrophages ascribed to MAF in various assays. A two signal hypothesis has been proposed in which MAF-I, as originally defined, serves as the priming factor and a second signal is responsible for the final triggering of "activation". Hibbs et al., (1977) *Science* 197:279; Ruco et al., (1978) *J. Immunol.* 121:2035; Meltzer, (1981) *Lymphokines* 3:319; and Schreiber et al., (1981) *Fed. Proc.* 40:1002).

To elicit in vitro tumoricidal cellular cytotoxicity by IFN-G-primed monocytes (macrophages), endotoxin represents the prototypic second or triggering signal. Pace et al., (1983) *J. Immunol.* 130:2011; Pace et al.,; (1983) *Proc. Natl. Acad. Sci. U.S.A.* 80:3782; Hibbs et al., (1977) *Science* 197:279; Ruco et al., (1978) *J. Immunol.* 120:2035; Meltzer, (1981) *Lymphokines* 3:319; Schreiber et al., (1981) *Fed. Proc.* 40:1002; Weinberg et al., (1978) *J. Immunol.* 121:72; Taramelli et al., (1980) *J. Immunol. Methods* 37:225; Schultz, (1982) *J. Interferon Res.* 2:459; and Pace et al., (1985) *J. Leuk. Biol.* 37:475. Contact with heat-killed *Listeria monocytogenes* can also suffice. Schreiber et al., (1982) *J. Exp. Med.* 156:677. Additionally, high doses of a lymphokine-containing medium, which need only be present for a short time, can trigger tumor cytotoxicity by IFN-G-primed monocytes (macrophages). Hibbs et al., (1977) *Science* 197:279; and Meltzer et al., (1982) *Fed. Proc.* 41:2198.

The role of cells of the monocyte-macrophage lineage as effector cells regulated by T cells can be obscured by the presence of a variety of agonists that directly elicit responses. Only after endotoxin, e.g. LPS, has been excluded from the in vitro analyses [Weinberg et al., (1978) *J. Immunol.* 121:72], can the inductive steps be resolved into at least two: priming and triggering [Meltzer, (1981) *Lymphokines* 3:319]. Priming can be accomplished in vivo by certain non-antigen specific as well as specific immunological stimuli such as Bacillus Calmette-Guerin (BCG) or in vitro by lymphokines elicited by T helper cells following stimulation with antigen or mitogen.

Recently, IFN-G has been identified as a necessary and sufficient agent for in vitro monocyte (macrophage) priming. Pace et al., (1983) *Proc. Natl. Acad. Sci. U.S.A.* 80:3782. It can replace the priming lymphokine preparation; and removal of IFN-G from priming lymphokine preparations removes the capacity to prime.

However, there is a general opinion based on current data that the priming activity of IFN-G is insufficient to fully elicit the tumoricidal capacity or cellular cytotoxicity of macrophages. Taramelli et al., (1980) *J. Immunol. Methods* 37:225. Available data are consistent with the requirement for another or "second" signal to trigger monocyte (macrophage) cytotoxicity, as exemplified by endotoxin.

Because endotoxin is a significant contaminant of most media and sera, investigators may inadvertently conclude that a priming lymphokine such as IFN-G alone is able to directly activate macrophage cytotoxicity [Weinberg et al., (1978) *J. Immunol.* 121:72], leading to the assignment of IFN-G as "macrophage-activating factor". This problem is made even more acute by the reciprocal enhancement of the responses of monocytes (macrophages) to priming lymphokine in the presence of minute amounts of endotoxin (e.g. LPS), and to endotoxin in the presence of small amounts of priming lymphokine. Pace et al., (1981) *J. Immunol.* 126:1863.

In contrast to the inability of priming lymphokine or IFN-G alone to complete monocyte (macrophage) activation for cytotoxicity, endotoxin at relatively high concentration (more than 1 ug/ml) is able to fully induce cytotoxicity without prior priming. Doe et al., (1978) *J. Exp. Med.* 148:544; and Cameron et al., (1980) *J. Immunol.* 124:708. However, the concentration of endotoxin required for the direct induction of the cellular cytotoxic function of monocytes and macrophages may elicit shock and disseminated intravascular coagulation in vivo. Ulevitch et al., (1984) *Fed. Proc.* 43:2755.

In a published report, Kornbluth et al., (1985) *Fed. Proc.* 44:1699, we reported that a lymphokine activity had been found that triggers human peripheral mononuclear cells (PBM) primed with IFN-G to express monocyte-mediated cytotoxicity of cultured human tumor cells. It was not then known whether the lymphokine activity found was due to a single molecule or a group of molecules either known or unknown acting in concert. The results discussed hereinafter illustrate that a single lymphokine molecule, designated by us as CTF, can provide the second, triggering signal that induces primed (stimulated) monocytes; i.e., macrophages, into cytotoxic activity.

BRIEF SUMMARY OF THE INVENTION

The present invention contemplates a substantially pure human proteinaceous lymphokine denominated cytotoxicity triggering factor (CTF), compositions containing CTF, a method for its use as well as a method for its preparation.

Substantially pure CTF is a protein having an apparent $M_r$ of about 55 kilodaltons (kd) as determined by gel exclusion chromatography using a gel matrix capable of fractionating proteins of an apparent relative molecular mass of about 6 to about 150 kd, and is capable of inducing secretion of a tumor cell-killing factor that includes tumor necrosis factor-alpha from interferon-gamma-primed peripheral blood mononuclear cells. The lymphokine is substantially free of pyrogen such as endotoxin as well as interferon-gamma, interleukin-2 and direct cytotoxin that are normally present (endogenous) when CTF is secreted. CTF is capable of secretion from differentiated allogeneically-stimulated normal human helper T cells such as those that express a T3+T4+T8−M1−phenotype.

Two additional substantially pure proteins are also contemplated. These pure proteins possess functional and purity characteristics that are substantially identical to the protein described above, but exhibit apparent relative molecular masses of about 14 kd and greater than about 150 kd when chromatographed on the above-identified matrix.

Another aspect of the invention is a method of inducing primed effector cells such as human monocytes to secrete a tumor cell-killing factor that includes tumor necrosis factor-alpha. Here, primed human effector cells are admixed in an aqueous medium with an aqueous composition containing substantially pure CTF present in an amount effective to trigger secretion of a tumor cell-killing factor that includes tumor necrosis factor-alpha. The tumor necrosis factor-alpha so obtained can be used as is or recovered.

Yet another aspect of this invention contemplates a method of inducing primed human effector cells such as monocytes to mediate the killing of tumor cells. Here, primed human effector cells such as PBM that provide a source of monocytes are admixed in an aqueous medium with an aqueous composition of substantially pure CTF in an amount effective to trigger secretion of a tumor-killing factor that includes tumor necrosis factor-alpha from the primed effectors. The tumor cells to be killed are contacted with the secreted tumor-killing factor.

In one embodiment of the above aspect of the invention, using monocytes as exemplary primable and primed cells of the effector cell population, the method is carried out in vivo, and the primed monocytes are within a tumor in the treated patient as are the tumor cells to be killed.

In one variant of this embodiment of this aspect of the invention, priming is carried out in vivo, while in another variant the priming is carried out in vitro. The in vivo priming can be accomplished by parenterally administering an amount of IFN-G that is sufficient to prime effector cells such as monocytes circulating in the patient's body. For in vitro priming, a preparation of about $1 \times 10^7$ cells per milliter of human leukocytes can be obtained as by leukapheresis and are primed by admixture and contact with a priming amount of IFN-G such as about 4 to about 200 U/ml, with the contact being maintained for about 36 to about 72 hours. The in vitro primed cells are then introduced into the patient's body, as by injection. The patient is maintained for a time period sufficient for the in vivo or in vitro primed monocytes to concentrate (migrate to and localize) in the tumor (in addition to those primed monocytes already present) and to clear from the patient's blood stream. Thereafter, a composition containing substantially pure CTF present in an aqueous physiologically tolerable carrier in an amount sufficient to trigger the tumor-concentrated primed monocytes is administered to the patient to trigger the concentrated primed monocytes to secrete the TNF-A-containing tumor killing factor.

In yet another embodiment, the method is carried out entirely in vitro, and the tumor cells contacted with the tumor-killing factor are supplied exogenously within about 10 hours of triggering the primed monocytes.

The present invention provides several benefits and advantages.

One benefit is that it provides a new lymphokine, CTF, that can be utilized to induce killing of tumor cells.

One advantage of the instant invention is that it provides a method of killing tumor cells that is selective, while leaving other cells unharmed.

Another benefit of the present invention is that it provides a further method for inducing primed monocytes to secrete tumor necrosis factor-alpha.

Still further benefits and advantages will be apparent to those skilled in the art from the detailed disclosure that follows.

Figure 1:
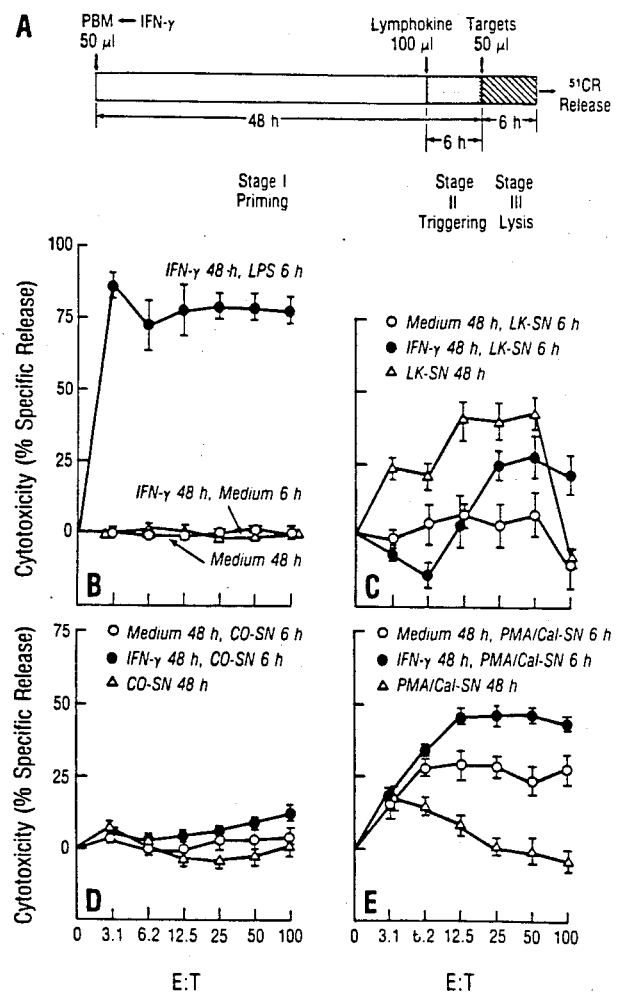
FIG. 1 contains a series of graphs (Panels A–E). Panel A is a schematic representation over time of a three-stage assay procedure used in conjunction with this invention to demonstrate the presence of cytotoxicity triggering factor (CTF). The left-hand portion (open) illustrates the 48-hour (48 h) in vitro priming step (stage I) of the assay in which 50 microliters (50 ul) of peripheral blood mononuclear cells (e.g., T cells, B cells, natural killer cells, monocytes) as a source of primable effector cells at concentrations of $2 \times 10^7$/milliliter to $6.25 \times 10^5$/milliliter (or purified blood monocytes at $5\times10^6$/milliliter to $1.25\times10^5$/milliliter) were cultured in round-bottomed microwells of a 96-well plate and maintained in the presence of 150 units/milliliter (U/ml) of IFN-G for 48 hours.

The first vertical line to the right of center indicates the time of admixture of 50–100 ul of lymphokine-containing medium or other cytokine preparation to the wells to trigger cytotoxic activity of the primed cells (stage II). After that admixture, the plate was thereafter returned to the incubator. This triggering stage lasted for a time period of 6 hours (6 h), and is represented by the dotted portion of the schematic.

The vertical line to the right of the above-mentioned vertical line indicates the initiation of the third, lytic, stage (stage III) at which time 50 ul of target ($^{51}$Cr-labeled) actinomycin (Act) D-treated WEHI 164 cells ($2\times10^5$/ml) were admixed with the IFN-G-primed and triggered cells. The space between the last-mentioned vertical line and the right-hand-most vertical line (hatched portion) represents the 6-hour in vitro lysis stage in which monocyte-dependent lysis of the target cells can occur.

The right-hand-most vertical line represents the time at which the assay is stopped, and the amount of $^{51}$Cr released into the supernatant due to cell lysis is determined, to indicate the presence of CTF.

Cell lysis was measured by removing one-half of the supernatant medium, admixing it with a scintillation cocktail and determining the counts per minute (CPM) in a liquid scintillation counter over a period of one minute. Data are reported as "% Specific Release", which is calculated as described in MATERIALS AND METHODS, Section V(E).

The graphs for Panels B, C, D and E illustrate cytotoxicity, or its lack, using the assay procedure described for Panel A, or a variant as described. Each ordinate is in units of Cytotoxicity (% Specific Release). Each abscissa is in units of the ratio of effector cells present (PBM for the illustrated analyses) to target cells present ($^{51}$Cr-labeled Act D-treated WEHI 164 cells)—E:T.

Panel B illustrates the effects of LPS triggering. A first set of points (●—●) illustrates that PBM incubated in medium alone for a time period of 48 hours failed to exhibit spontaneous monocyte-mediated cytotoxicity. A second set of points (Δ—Δ) illustrates that PBM incubated in medium that also contained 150 U/ml of IFN-γ for a time period of 48 hours also failed to exhibit spontaneous moncyte-mediated cytotoxicity. The third set of points ( — ) illustrates that PBM incubated in medium containing 150 U/ml of IFN-γ for a time period of 48 hours to which were added 10 micrograms/-milliliter of LPS mediated profound cytotoxic activity during the 6-hour lytic stage of the above assay. This assay permits identification of primed monocytes/macrophages, and demonstrates that unprimed monocytes/-macrophages can be primed by IFN-γ.

Panel C illustrates triggering induced by lymphokine-containing supernatant (LK-SN) under three conditions. One set of points (●—●) illustrates that PBM incubated in medium [described in MATERIALS AND METHODS Section V(A)] for 48 hours (unprimed) followed by a 6 hour incubation in LK-SN failed to induce cytotoxicity. A second set of points ( — ) illustrates that a 6 hour incubation of PBM primed by prior incubation with 150 u/ml of IFN-G for 48 hours induces significant monocyte cytotoxicity. The third set of points (Δ—Δ) illustrates that LK-SN, which contains both IFN-G and CTF, induces monocyte cytotoxicity when incubated with PBM effectors for 48 hours.

Panel D illustrates the lack of triggering induced by control-supernatant (CO-SN; medium from unstimulated human PBM) under three conditions. The graphs of this panel show that the triggering lymphokine is not a constitutive product of cultured unprimed PBM or cultured Daudi cells used to stimulate PBM. One set of points (●—●) illustrates a lack of cytotoxicity when effector cells were incubated with medium for 48 hours followed by incubation in CO-SN for 6 hours. A second set of points ( — ) illustrates a lack of cytotoxicity when effectors were incubated with 150 U/ml of IFN-G for 48 hours followed by a 6 hour incubation with CO-SN. The third set of points (Δ—Δ) illustrates a lack of cytotoxicity when effector cells were incubated for 48 hours with CO-SN.

Panel E illustrates that stimulation of lymphocytes produces a triggering lymphokine. A first set of points (O—O) illustrates the effects where nylon wool-enriched T cells from the usually used PBM were chemically stimulated with a 3 hour pulse of 10 nanograms/-milliliter (ng/ml) of phorbol myristate acetate (PMA) and 1 micromolar (uM) of calcium ionophore A23187. After 48 hours of stimulating incubation, supernatant medium was concentrated 10-fold, fractionated on a Sephadex G-100sf column, and the 55 kd fraction was collected. That fraction (PMA/CaI-SN) induced monocyte cytotoxicity in PBM maintained in medium for a time period of 48 hours in the absence of IFN-G priming, although to a lesser extent than with priming by IFN-G. (It is noted that this result is affected by the presence of PMA carryover and by contaminant LPS.) A second set of points (●—●) illustrates that priming the effectors by a 48 hour incubation with 150 U/ml of IFN-G in medium followed by a 6 hour incubation with PMA/CaI-SN as the second signal provided significantly increased cytotoxicity. The third set of points (Δ—Δ) illustrates that the cytototoxicity shown after a 6 hour incubation with PMA/CaI-SN decreases with a 48 hour incubation with PMA/CaI-SN alone.

Figure 2:
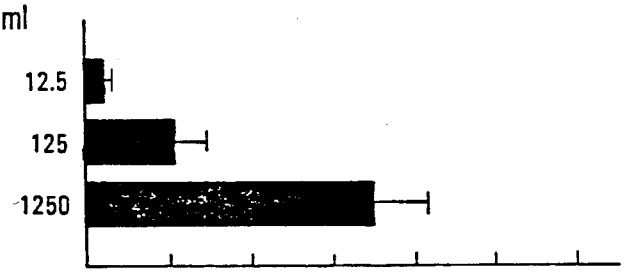
Figure 2:
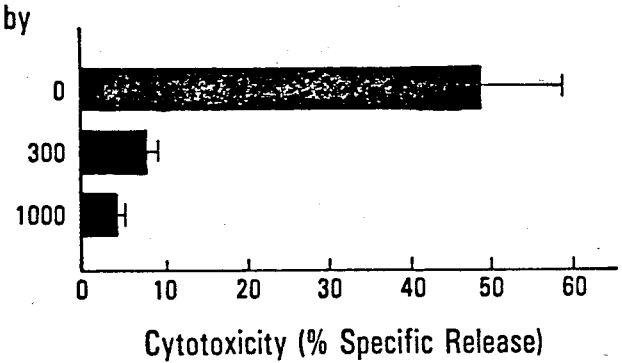

FIG. 2 contains two panels that illustrate the role of tumor necrosis factor-alpha (TNF-α;TNF-A) in cytotoxicity using PBM as a source of effector cells. Panel A illustrates that incremental amounts of TNF-α admixed with IFN-G-containing media induced cytotoxicity in Act D-treated WEHI 164 target cells in the 6 hour lysis assay. The E:T ratio was 50:1. The abscissa is in units of cytotoxicity (% Specific Release), while the ordinate is in units of TNF-α added per milliliter (TNF-α U/ml).

Panel B illustrates the decrease in Cytotoxicity (% Specific Release) induced in IFN-G-primed PBM admixed with LK-SN when a monoclonal antibody that binds to and neutralizes TNF-A was also present in the admixture. The E:T ratio was 50:1. The ordinate is in units of TNF-A activity capable of inhibition by incremental amounts of the monoclonal antibody added per milliliter (Units of TNF-α Inhibited by MAb/ml).

Figure 3:
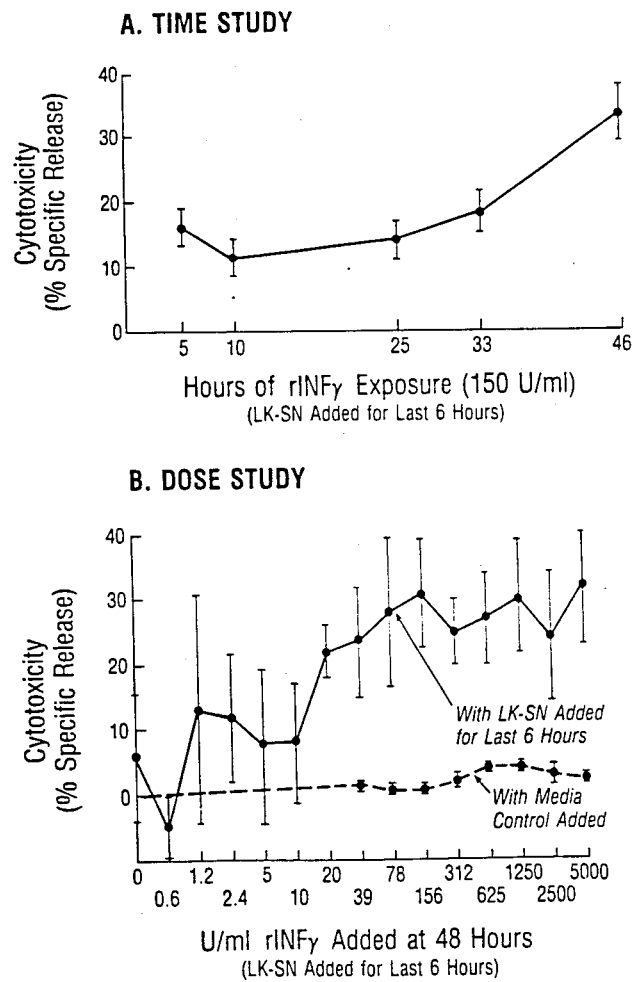

FIG. 3 contains two panels that illustrate the kinetics (Time Study) and dose response (Dose Study) for IFN-G priming of PBM as the effector cell-containing population. Here, dose and time requirements were assessed for IFN-G priming of cytotoxicity induced by a constant 30 percent LK-SN for 6 hours of stage II triggering (LK-SN Added for Last 6 Hours) using a 50:1 PBM:target cell ratio.

As is seen in Panel A, the response to a constant amount (150 U/ml) of recombinant IFN-G (rIFN-γ) was maximal at 46 hours of incubation.

The results of Panel B were obtained using a 48 hour priming with using varying amounts of recombinant IFN-G (U/ml rIFN-γ Added at 48 Hours). Minimal priming was obtained at about 4–20 U/ml, while maximal priming was obtained at greater than 20 U/ml and was relatively constant thereafter over the range studied. The dashed line (---) illustrates that IFN-G alone did not induce cytotoxicity.

Figure 4:
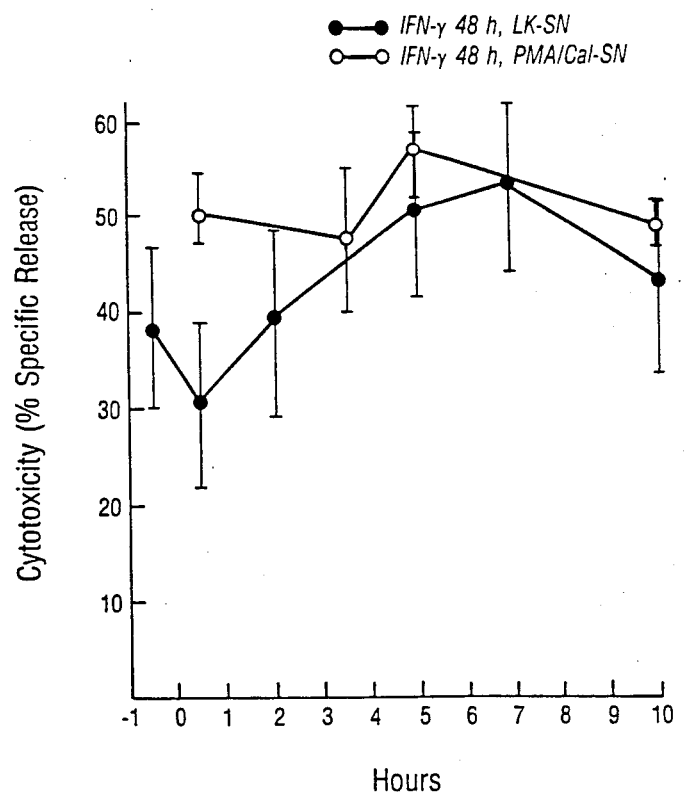

FIG. 4 contains a single graph and illustrates the temporal requirements for triggering of cytotoxicity by CTF. PBM primed by incubation with IFN-G for 48 hours were contacted and maintained with CTF-containing compositions (●—●, LK-SN; and O—O, PMA/CaI-SN) for the durations indicated by the graph points during stage II of the assay. The data illustrate that triggering was rapid regardless of the source.

Figure 5:
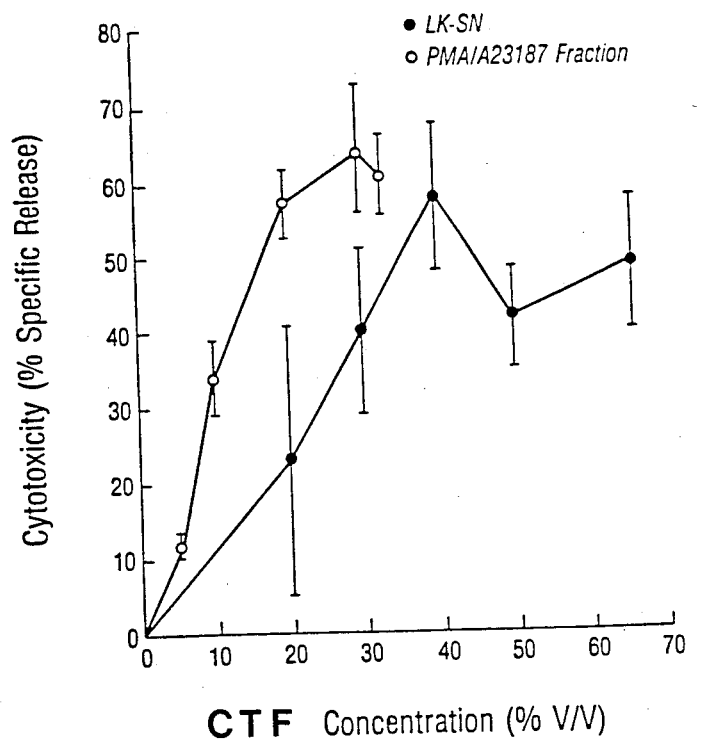

FIG. 5 contains a single graph that illustrates a quantititative assay of CTF. Serial dilutions of CTF-containing preparations were admixed at stage II of the CTF assay of FIG. 1 to form cultures containing 0.1 milliliter, and the cultures so prepared were maintained for a period of 6 hours using PBM that had been primed with 150 U/ml IFN-G for 48 hours, and at an E:T ratio of 50:1. CTF was quantitated in one-half maximal units. Titers of CTF differed markedly depending upon the method used for production. The LK-SN preparation contained more than 100 U/ml of IFN-G, while the PMA/A23187 Fraction lacked IFN-G by RIA assays.

Figure 6:
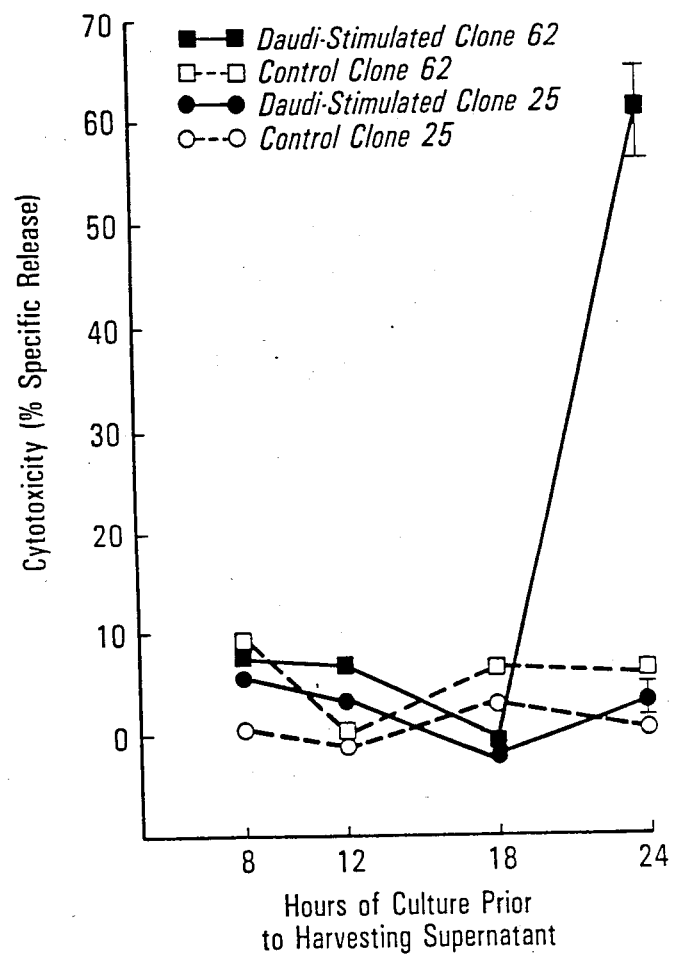

FIG. 6 contains a single graph that illustrates inductive requirements for production of CTF by T cell clones. Human T helper clones from normal donors specifically responsive to the HLA-DR alloantigens of irradiated Daudi cells were cocultured with irradiated Daudi cells at a 1:4 T:Daudi ratio. Culture medium supernatant was collected at intervals to analyze kinetics of CTF production (■Daudi-stimulated clone 62; ● Daudi-stimulated clone 25). Control supernatants (□ control clone 62; O control clone 25) were generated in parallel in autologous cultures of T cell clones with irradiated Daudi cell stimulation, and were mixed at 1:4 T cell to Daudi cell supernatant before use.

The results shown in the graph illustrate that coculture of clone 62 with irradiated Daudi cells induced CTF secretion at 24 hours, while similar CTF secretion was absent from the controls. CTF was not secreted from coculture of clone 25 with irradiated Daudi cells, although that clone did secrete interleukin-2.

Figure 7:
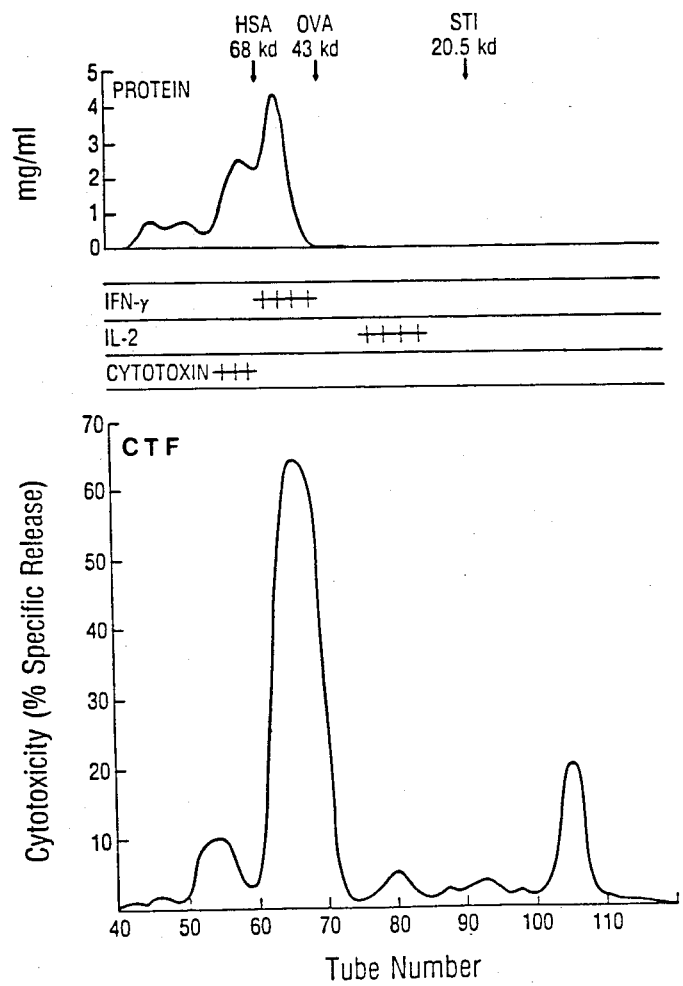

FIG. 7 illustrates resolution of CTF by molecular exclusion chromatography. A composite of data from four chromatographic fractionations of CTF-containing LK-SN and PMA/CaI-SN preparations on Sephadex G-100sf is represented. The presence of CTF was assayed using column fractions to trigger IFN-G-primed PBM in a 6 hour incubation using the assay illustrated in FIG. 1. Other activities were assayed as described hereinafter. The predominant form of CTF eluted with an $M_r$ of approximately 55 kilodaltons (kd). The relative proportions of the less active peaks (about 14 kd and greater than about 150 kd) varied depending on the induction protocol. IFN-G was not separated from CTF by the chromatographic procedure.

DETAILED DESCRIPTION OF THE INVENTION

Abbreviations

Act D=actinomycin D
CaI=calcium ionophore A23187
CO-SN=control supernatant medium
CTF=cytotoxicity triggering factor
FBS=fetal bovine serum
GM-CSF=granulocyte-monocyte colony stimulating factor
HEPES=N-2-hydroxyethylpiperazine-N-2-ethanesulfanic acid
IL=interleukin
IFN=interferon
IFN-G=interferon gamma
LK-SN=lymphokine-containing supernatant medium
LPS=bacterial lipopolysaccharide
MPIF=monocyte procoagulant-inducing factor
PBM=peripheral blood mononuclear cells
PBS=phosphate-buffered saline
PMA=phorbol myristate acetate
SDS=sodium dodecyl sulfate
TNF-A=tumor necrosis factor-alpha
TNF-B=tumor necrosis factor-beta

I. Introduction

The present invention utilizes "effector cells" that when primed are capable of secreting tumor necrosis factor-alpha (TNF-A) after triggering by a proteinaceous lymphokine that is referred to herein as CTF. An effector cell of the present invention is therefore defined as a cell or cell population that is (1) capable of priming by interferon-gamma (IFN-G), and (2) triggered by contact with a composition containing CTF, wherein triggering is defined hereinafter using bacterial lipopolysaccharide (LPS).

Effector cells include cells of the peripheral blood mononuclear (PBM) cell group that itself includes T cells, B cells, natural killer cells and monocytes, as already noted. Monocytes are one class of PBM that the results discussed hereinafter illustrate are both primable and triggerable, as discussed above and in further detail hereinafter. Monocytes circulate in the blood and mature by a pathway that is not completely known into macrophages that settle into various body tissues. Monocytes are utilized herein as exemplary effector cells, and are often referred to herein as "monocytes/macrophages" or as "monocytes (macrophages)" to illustrate the relatedness of the two cell types.

To investigate the effects of IFN-G on the induction of vigorous human monocyte cytotoxicity, a recently described assay for drug-dependent cellular cytotoxicity has been adopted and modified. Ziegler-Heitbrock et al., (1984) *J. Natl. Cancer Inst.* 72:23; and Colotta et al., (1984) *J. Immunol.* 132:936. This assay, as modified herein, selectively identifies and quantifies human effector cell-mediated, e.g., monocyte-mediated, in vitro tumoridical activity (cytotoxicity).

It is found that if peripheral blood mononuclear cells (PBM), which include T cells, B cells, natural killer (NK) cells, and monocytes, or purified monocytes alone are isolated and assayed under substantially pyrogen-free (endotoxin-free; less than about 0.01 ng/ml of LPS) conditions, cytotoxic effector function is latent, but can be rapidly induced by endotoxin. In the absence of endotoxin, other physiologic signals including lymphokines capable of inducing monocyte activation for cellular cytotoxicity can be identified and characterized.

The existence and characterization of a new lymphokine that can serve as the second or triggering signal to selectively induce the expression of vigorous monocyte cytotoxicity by primed effector cells [Kornbluth et al., (1985) Fed. Proc. 44:1699] is demonstrated by the results described hereinafter. In this pathway, IFN-G alone is insufficient to induce cytotoxicity; however, prolonged exposure to IFN-G primes effector cells for the triggering action of a second signal provided by the substantially pure proteinaceous lymphokine of this invention that is designated cytotoxicity triggering factor (CTF).

CTF alone is not effective and sufficient to induce monocytes to express cytotoxicity. PBM containing effector cells such as monocytes primed with IFN-G are sensitive to triggering by CTF. CTF alone at high concentration (above 100 units per milliliter) has been observed to induce cytotoxicity that may be due to the presence of small amounts of endotoxin, the PMA and/or calcium ionophore used to stimulate the T cells to produce CTF, or another contaminant. The CTF-induced cellular cytotoxicity that results is believed attributable to and requires the direct effects of tumor necrosis factor-alpha (TNF-A), a monokine; i.e., a product of monocytes/macrophages, with several known biological effects. Old, (1985) Science 230:630.

By describing the immunological production of CTF by T lymphocytes as well as by cloned normal T helper cells, a physiological pathway is delineated for the production of TNF-A-dependent tumoricidal activity where CTF serves as the dominant control element, and an endogenous equivalent to exogenous endotoxin in inducing TNF-A secretion from human monocytes. In addition to further resolving the complexity of the MAF controversy and the function of the immune response, the substantially pure CTF provides a means for inducing TNF-A production by INF-G-primed monocytes/macrophages in vivo.

For the examination of human mononuclear phagocyte cytotoxicity, peripheral blood monocytes are most readily available and represent a pool of circulating cells, including effector cells, that migrate to inflammatory sites when properly recruited. Modifying a recently developed rapid assay that is specific for monocyte-mediated cytotoxicity; i.e., $^{51}$Cr released from Act D-treated WEHI 164 murine fibrosarcoma targets, the requirements for both priming and triggering of the human monocyte for tumoricidal activity were analyzed.

Contrary to the initial reports for this assay, monocytes present in PBM from normal subjects (persons free from disease, inflammatory disorders and tumors) have consistently lacked significant spontaneous cytotoxic activity. Instead, it would appear that the minute amount of endotoxin commonly found in culture media, sera and separating solutions is quite sufficient to rapidly induce profound monocyte-mediated cytotoxicity of target cells. The addition of as little as 0.001 ng/ml of LPS to culture solutions can provoke the described responses. Since endotoxin is not physiologically present in quantities sufficient to induce monocyte cytotoxicity, the prior assay was modified as described hereinafter to a prolonged three-stage analytical system to search for and find the immunologically relevant second signal or triggering lymphokine.

II. CTF: An Overview

The capacity of IFN-G to serve as a sole MAF; i.e., induce monocyte cytotoxicity, was extensively explored with both natural and recombinant proteins. Whether present for 6 through 72 hours, added once or added repeatedly, or used in doses from 0.1 to 10,000 U/ml, IFN-G alone has reproducibly failed to activate effector cells in PBM populations for monocyte-mediated cytotoxicity. However, IFN-G (150 U/ml for 48 hours) was found to cause effector cells in PBM to become more than 30 times more sensitive to endotoxin as a second signal that triggers cytotoxicity. Similar results have been described for murine macrophages by Pace et al., (1981) J. Immunol. 126:1863.

Since lymphokine preparations containing a crude "MAF" had been shown to effectively activate monocytes [Kleinerman et al., (1983) Lymphokine Res. 1:7; Kleinerman et al., (1985) Cancer Res. 45:2058; and Kleinerman et al., (1984) J. Immunol. 133:4], the abilities of a variety of lymphokine-containing media were examined for the capacity to induce cytotoxicity against Act D-treated WEHI 164 cells. Two media types and methods of their use to induce cytotoxicity are discussed in detail hereinafter as is a third cell type and medium that are undergoing further characterizing studies.

Initially, early Daudi cell-stimulated culture media (lymphokine-containing supernatant medium; LK-SN) that contained IFN-G, IL-2, migration inhibitory factor (MIF) and monocyte procoagulant inducing factor (MPIF) were used. Gregory et al., (1984) Fed. Proc. 43:1748. Although LK-SN possessed considerable activity, it did not directly induce monocyte-mediated cytotoxicity in a 6 hour induction period.

Hibbs et al., (1977) Science 197:279 and Meltzer and colleagues [Meltzer, (1981) Lymphokines 3:319; and Meltzer et al., (1982) Fed. Proc. 41:2198] have observed enhanced effects of sequential additions of crude MAF. The combined effects of IFN-G as a first priming signal and LK-SN as a second signal were analyzed in the present study.

IFN-G was used at a concentration and time (150 U/ml for 48–72 hours) reported to enhance monocyte $H_2O_2$ production [Nakagawara et al., (1982) J. Clin. Invest. 70:1042; and Gately et al., (1983) J. Immunol. 131:2583], oxygen-dependent and -independent killing of intracellular Leishmania donovani [Murray et al., (1983) J. Clin. Invest. 72:1506], and expression of IL-2 receptors [Herrmann et al., (1985) J. Exp. Med. 162:1111]. Effector cells in PBM primed by IFN-G under these conditions expressed potent monocyte-mediated cytotoxicity in the Act D-treated WEHI 164 assay, but only when subsequently triggered by LK-SN. The observed triggering was not attributable to endotoxin contamination of the LK-SN since the control supernatants (CO-SN) included media from separate culture of the same cells used to make the LK-SN but the media were mixed rather than the cells; and all media and sera were devoid of detectable endotoxin [less than 10–30 picograms per milliter (pg/ml)].

LK-SN that failed to induce monocyte cytotoxicity in 6 hours, in selected preparations, did induce cytotoxicity in 48 hours. Since these LK-SN contained IFN-G, prolonged exposure to these LK-SN could both prime monocytes and then trigger them. Had 48 hours been used as the only time point for such selected LK-SN addition, the rapid effect of a non-IFN-G MAF on IFN-G-primed monocytes would not have been apparent, and would have remained overlooked.

We have found that MAF-containing preparations made by the method of Kleinerman and Fidler, (1983) *Lymphokine Res.* 1:7 (the supernatant medium from PBM stimulated for 48 hours with Concanavalin A-Sepharose) contain both IFN-G (more than 300 U/ml) and the secondary triggering lymphokine. When monocyts are treated with this complex MAF preparation for 48 hours, or when prolonged cytotoxicity assays are used (that permit prolonged and multiple biological effects during the assay), the temporal dissociation between the priming effect of IFN-G and the triggering effect of the second more rapidly acting lymphokine cannot be distinguished.

Since IFN-G was the first molecule identified as a MAF and must act first on effector cells in PBM such as monocytes in order to prime them, it is often referred to herein as MAF-I. The second lymphokine that acts rapidly and is effective on IFN-G-primed monocytes represents an IFN-G cofactor that is designated as cytotoxicity triggering factor (CTF). The CTF molecule is consistent with an immunologic analog for endotoxin since it triggers IFN-G-primed cells.

CTF is not IFN-G since it cannot be replaced by IFN-G (Table I, hereinafter in RESULTS Section IV). Additionally, when LK-SN was passed through an affinity column containing an excess of anti-IFN-G monoclonal antibodies, IFN-G was removed (less than 1 U/ml remaining by RIA), yet CTF activity remained. Finally, a relatively high concentration CTF-containing medium has been prepared by chemically stimulating nylon wool-purified normal T cells, and the resulting substantially pure preparation of CTF substantially lacks IFN-G (less than 1 U/ml by RIA), although it is a potent source of CTF.

Since these studies began, Krammer and colleagues, [Gemsa et al., (1984) *Mol. Immunol.* 21:1267; and Hamann et al., (1985) *Eur. J. Immunol.* 15:18] have reported the existence of a preparation they refer to as macrophage cytotoxicity-inducing factor-2 (MCIF-2) that acts in concert with IFN-G to induce cellular cytotoxicity in murine macrophages. In addition to inducing tumoricidal activity, MCIF-2 or one or more constituent molecules is reported to act in concert with IFN-G to induce intracellular schistosomulicidal activity. Krammer et al., (1985) *J. Immunol.* 135:3258.

There are other recent reports of non-IFN-G cytotoxicity factors that are said to induce cytotoxic activity [Erickson et al., (1982) *Cell. Immunol.* 72:195; Meltzer et al., (1982) *J. Immunol.* 129:2802; Meltzer et al., (1985) *Fed. Proc.* 44:1697a; and Kleinerman et al., (1984) *Cancer Res.* 44:4470], antibody-dependent cellular cytotoxicity [Ralph, (1985) *Lymphokine Res.* 3:153], anti-Leishmania activity [Hoover et al., (1985) *Fed. Proc.* 44:1697a; and Buchmuller et al., (1985) *Cell. Immunol.* 90:242], resistance to Herpes virus replication in macrophages [Rose et al., (1985) *Fed. Proc.* 44:1697a], macrophage production of IL-1 [Amento et al., (1985) *J. Immunol.* 134:350; and Dinarello et al., (1985) *J. Leukocyte Biol.* 37:697a], and monocytic differentiation of leukemia cells [Dayton et al., (1985) *Blood* 66:583]. The relationship of these factors to CTF, if any, cannot yet be resolved.

More recently, Lee et al., (1986) *J. Immunol.* 134:1322 reported the identification and characterization of a human T cell-derived lymphokine with MAF-like activity distinct from that of IFN-G. That study utilized twelve T cell lines all but one of which were transformed by HTLV-I virus.

The report indicated that five cell lines produced culture supernatants that contained mediators that activated human monocytes to kill A-375 human melanoma cells. The presence of IFN-G in the supernatants of two cell lines that exhibited cytotoxicity was reported, as were the effects on cytotoxicity and monocyte activation of a supernatant of one of those two cell lines. Admixture of excess anti-IFN-G monoclonal antibodies with that supernatant reportedly decreased monocyte activation by exogenous IFN-G, but had no inhibitory effect on activation of monocyte tumoricidal activity induced by supernatants from that cell line.

In the assay system utilized herein, IFN-G and CTF appear to act on the monocyte sub-population of PBM cells since: (1) they do not induce cytotoxicity in PBM populations depleted of monocytes; (2) isolated monocytes are as effective as the same number of monocytes present in PBM; (3) the cytotoxicity factor TNF-A is a product of monocytes; and (4) microscopically viewed killing of tumor cells was observed where monocytes were attached to tumor cells. While at least cells of the monocyte lineage are thus implicated as the effector cells in mediated cytotoxicity induced by CTF, the precise cell sub-type or sub-types responsible for that cytotoxicity is presently unknown. Without wishing to be bound by any one theory, it is thought that at least monocytes are primed as by IFN-G, and that the primed monocytes are the effector cells that mediate cytotoxicity. This is not to imply that one or more additional cell type or types is not also capable of CTF-induced cytotoxicity. For example, the method of depletion of monocytes from PBM populations also depleted natural killer cells, and natural killer cells co-isolated partly with monocytes.

For convenience herein, the cells that are primable for CTF-mediated cytotoxicity are referred to as effector cells or monocytes, and the primed cells from the heterogeneous mixture that constituted the usually used unprimed PBM are referred to broadly as primed effector cells, and more specifically as primed monocytes or primed macrophages. Monocytes and macrophages are distinguished from each other in that monocytes circulate while macrophages are the progeny of monocytes that are found localized in tissues. In the detailed studies described herein, where effector cells in PBM are primed to form cytotoxic-mediating effector cells, the number of effector cells referred to in effector:target cell ratios are the total number of PBM added to the culture medium, and not just cells present that are of the monocyte lineage; the PBM are thus considered to be 100 percent primed for those studies.

Upon finding that primed effector cells in PBM such as primed monocytes could mediate cytotoxicity in the absence of LPS, the molecular identity of CTF and the mechanism by which cytotoxicity were effected were sought.

As detected in the assay described herein, CTF follows a sigmoidal dose response that allows it to be quantitated in half-maximal units, as discussed in Pace et al., (1981) *J. Immunol.* 126:1863. In a kinetic study, CTF appears to act very quickly, and is even effective when added concurrently with the target cells during the final 6 hour lytic phase of the assay.

Analysis of the medium from cloned normal T cells indicates that CTF can be a normal T helper cell product that is not a constitutive product, but can be produced following stimulation of a minor subpopulation of normal T helper clones with an alloantigen. CTF appears to be a differentiation-dependent product of the normal T cell lineage. CTF is also a product of certain transformed T cells as is discussed hereinafter.

CTF elutes from Sephadex G-100sf (super fine) in a peak of about 55 kilodaltons (kd) (about 50 to about 60 kd), which is well separated from IL-2. Minor peaks of about 14 kd (about 9 to about 19 kd) and of greater than about 150 kd are also seen that exhibit CTF activity.

IL-2 lacks CTF activity in the described assay. IL-1 has been reported to induce monocyte cytotoxicity [Onozaki et al., (1985) J. Immunol. 135:314]. However, IL-1 alpha and beta have no significant effects at concentrations up to 50 U/ml in the described assay. Recombinant colony stimulating factor-1 (rCSF-1) has also been evaluated for CTF activity and found to be lacking, as were the about 55 kd and about 14 kd CTF fractions lacking in CSF-1 activity. Additionally, the 55 kd form of PMA/CaI-SN CTF lacked TNF-A or lymphotoxin (TNF-beta) activity in the highly sensitive L929 cell assay. Thus, CTF is also not one of those well characterized cytokines.

CTF is thus a T cell product that can induce TNF-A secretion by primed monocytes in 6 hours to provide levels of greater than 300 units per milliliter with PBM at $2.5 \times 10^6$ cells/ml, the approximate PBM concentration of normal blood. Such TNF-A induction indicates a physiological role for CTF that is fundamental to the T cell-instructed limb of the immune response, and establishes that role as a fundamental property beyond stimulating primed human effector cells in human PBM to mediate cytotoxicity to the drug-treated murine fibrosarcoma cell line used in these studies.

Since IFN-G has been reported to enhance the cytotoxic effect of TNF-A on target cells [Williamson et al., (1983) Proc. Natl. Acad. Sci. U.S.A. 80:5397; and Stone-Wolff et al., (1984) J. Exp. Med. 159:828], it was considered that the apparent priming effect of IFN-G could have been due to this interaction. While such an interaction may occur, priming of effector cells in human PBM requires more than 24 hours of IFN-G exposure, which makes direct effects of the effector cells more likely, and addition of IFN-G as the second signal, thus fully permitting its effects on the target cell, was not associated with cytotoxicity.

While IFN-G was shown not to be associated with cytotoxicity aside from its ability to prime the effector cells, TNF-A was shown to be a required agent mediating cytotoxicity. Thus, all induced cytotoxicity was abrogated by admixture of monoclonal antibodies that specifically neutralize the activity of TNF-A to a primed culture of effector cell-containing PBM prior at the lytic stage of the assay described herein. That abrogation of cytotoxicity demonstrates that the CTF-mediated effect is TNF-A-dependent.

TNF-A has been shown to have cytostatic and cytotoxic activity against a wide variety of human tumor cell lines with an average sensitivity of about 32-64 units/milliliter (U/ml), although TNF-A-resistant tumor cells are known. Old, (1985) Science 230:630. By contrast, normal fibroblasts are unaffected by TNF-A. TNF-A can stimulate human neutrophil functions [Shalaby et al., (1985) J. Immunol. 135:2069]; can be detrimental to the host by inducing cachexia [Torti et al., (1985) Science 229:867], and it mediates toxicity induced by LPS in vivo [Beutler et al., (1985) Science 229:869].

To the extent that CTF induces secretion of TNF-A in vivo, it may participate in the host defense and pathogenetic sequence of certain disease states. Since CTF is selectively active in triggering TNF-A secretion from IFN-G-primed effector cells in human PBM, administration of CTF at relatively low doses preferentially triggers local secretion of a TNF-A-containing factor at sites of local inflammation and immune responses, generating significant local or systemic levels of IFN-G.

Tumors often contain significant numbers of macrophages and other cells of the immune syustem [Russell et al., (1980) Contemp. Top. Immunol. 10:143] that are inordinately sensitive to the cytotoxicity-triggering action of LPS and are indistinguishable from IFN-G-primed macrophages [Russell et al., (1977) J. Exp. Med. 146:1511]. Physiological host responses have thus apparently primed intratumoral macrophages, but have not triggered them. Relatively small doses of CTF at more modest concentrations are thought to provide cytotoxicity of tumor cells by inducing local biosynthesis of a TNF-A-containing tumor cell-killing factor within the tumor, as well as other biologically comparable responses, without the whole body side effects observed with the administration of TNF-A itself, e.g., shock.

III. Substantially Pure CTF

The present invention relates to a novel, substantially pure proteinaceous lymphokine referred to as cytotoxicity triggering factor (CTF), its methods of production and to methods of its use.

CTF is a proteinacious lymphokine that is capable of secretion from differentiated, stimulated normal human helper T cells such as those that express a T3+T4+T8−M1− phenotype. When expressed from those and other studied T cells, the protein has an apparent relative molecular mass ($M_r$) determined by gel exclusion chromatography on Sephadex G-100sf, a gel matrix having a capacity to fractionate proteins of an apparent relative molecular mass of about 4000 to about 150,000 daltons, of about 50 to about 60 kilodaltons (kd), that is conveniently expressed as about 55 kd or as 55±5 kd.

As noted earlier, CTF molecules with apparent relative molecular masses of about 14±5 kd and greater than about 150 kd were also eluted from the Sephadex G-100sf column. The relation of those molecules to the species of $M_r$ 55 kd is presently unknown.

Substantially pure CTF is endotoxin-free. The most frequently found endotoxin contaminant is bacterial lipopolysaccharide, LPS. Freedom from endotoxin can be conveniently assayed using the well known Limulus amoebocyte lysate or the USP Pyrogen Test assays described hereinafter.

In preferred practice, an aqueous composition containing a triggering amount of substantially pure CTF contains less than about 0.01 ng/ml of LPS or other pyrogen. More preferably, such a composition contains less than about 0.001 ng/ml. Examined differently, substantially pure CTF most preferably contains less than about 300 femtograms of endotoxin (pyrogen) per unit, where one unit of CTF is present in less than 2 nanograms of substantially pure CTF.

The substantially pure CTF is also substantially free of IFN-G; i.e., it contains less than a monocyte-activating amount of IFN-G. IFN-G, if present, can conveniently be removed by use of an immmunosorbant column that contains antibodies that selectively bind to IFN-G. Exemplary amounts of IFN-G that can be present (non-priming amounts) are typically less than about 0.1 units of IFN-G per unit of CTF. The presence of a priming amount of IFN-G in substantially pure CTF can be assayed by admixture of a triggering amount of CTF with effector cell-containing PBM and culturing of the admixture for at least 24 hours, and more preferably 48 hours, followed by admixture of labeled, target Act D-treated WEHI 164 cells, and assaying for target cell lysis using the techniques described for the lytic assay that are described hereinafter. An absence of triggering indicates an absence of IFN-G.

The presence of direct cytotoxin can be assayed using the sensitive L929 cell assay described by Armstrong et al. (1985) *J. Natl. Canc. Inst.* 74:1. A 70 kd cytotoxin that is produced in LK-SN can be removed from CTF preparation by chromatography on Sephadex G-100sf. This cytotoxin was absent from preparations of CTF using the PMA/CaI-SN protocol.

TNF-A is another direct cytotoxin that is also absent from substantially pure CTF. When present, as determined by the above L929 cell assay, TNF-A can also be removed by chromatography on Sephadex G-100sf. TNF-A is typically not present if the established T cell lines discussed in Section IV(H) are utilized for production of CTF.

Substantially pure CTF is also substantially free of lymphotoxin (TNF-beta or TNF-B). CTF obtained from LK-SN sometimes contained a direct cytotoxin that may have been TNF-A or TNF-B, while CTF obtained from PMA/CaI-SN did not contain this cytotoxin. Regardless of its identity, this sometimes observed cytotoxin can be removed by fractionation on Sephadex G-100sf, where the 14, 55 or greater than 150 kd fractions containing CTF are obtained and used.

The approximately 70 kd cytotoxin, TNF-A and TNF-B (lymphotoxin), unless specified, are referred to herein collectively as "direct cytotoxin". Substantially pure CTF is substantially free of direct cytotoxin.

Absence or substantial freedom of endogenous 70 kd cytotoxin, TNF-A and TNF-B can be assayed by admixture of a triggering amount of CTF with the above L929 cells or with target Act D-treated WEHI 164 cells, or similar procedures as are well known in the art.

Substantially pure CTF is also free of interleukin-2. IL-2 was not detected in PMA/CaI-SN, but was present in LK-SN. Chromatography on Sephadex G-100sf removes IL-2 from aqueous CTF preparations as is seen in FIG. 7, and can be utilized to detect the presence of IL-2. IL-2 can also be removed by the described purification from cell lines or by affinity chromatography as described by Altman et al. in co-assigned U.S. patent application Ser. No. 597,179 filed April 5, 1984.

Substantially unglycosylated CTF as obtained from PBM or the described established cell lines discussed hereinafter cultured in tunicamycin is also contemplated herein and can also be in substantially pure form as described hereinabove.

Substantially pure CTF preferably has an activity of at least about 50,000 units per milligram of total protein, and more preferably at least about 100,000 units/milligram. Most preferably, substantially pure CTF has an activity of at least about 300,000 units per milligram of total protein.

Substantially pure CTF is useful in a method of inducing primed human effector cells such as monocytes to secrete a tumor cell killing factor that includes TNF-A. In this method, for example, primed human monocytes are admixed and contacted in an aqueous medium with an aqueous composition containing substantially pure CTF that is present in an amount effective to trigger secretion of a tumor cell-killing factor that includes TNF-A. The aqueous medium in which the admixture and contact take place can be an in vitro cell culture medium containing cells and a supernatant, or in vivo in the aqueous medium provided by a treated host's blood and lymph systems.

The TNF-A from the tumor cell-killing factor so secreted can be recovered by usual means such as passage of an in vitro culture supernatant through a sizing column such as a column containing Sephadex G-100sf, or through an affinity column containing an antibody directed to TNF-A as immunosorbant followed by elution from the column. An in vitro preparation can also be utilized as is. TNF-A produced in vivo is typically utilized in situ as described below.

The above method can be carried out in vitro or in vivo.

In vitro practice of the method is exemplified in the assay system and related discussion discussed in detail hereinafter. In typical usage, PBM at about $6 \times 10^5$ to about $2 \times 10^7$ cells per milliliter are cultured and the effector cells therein are primed, and a triggering amount, e.g., about 3 to about 300 units per milliliter, of substantially pure CTF is admixed. The cell culture so prepared is maintained for a time period sufficient for the tumor cell-killing factor containing TNF-A to be secreted from the primed, triggered cells. An exemplary time period for that maintenance is about 6 hours.

The tumor cell-killing factor secreted by triggered, primed human effectors such as monocytes (macrophages) includes TNF-A as a constituent, and may include other proteinaceous and non-proteinaceous materials as well. As discussed in relation to FIG. 2, the presence of TNF-A in in vitro secretions can be assayed using antibodies directed to TNF-A. The presence of TNF-A secreted in vivo is inferred by the killing of tumor cells.

In vivo practice of the above method is typically carried out in a patient having a tumor and is described below.

Substantially pure CTF is useful in a method of inducing primed human effector cells such as monocytes (macrophages) to mediate tumoricidal activity (kill tumor cells) in vivo and in vitro. In accordance with this method, an aqueous composition of substantially pure CTF is admixed in an aqueous medium with primed human effector cells in an amount effective to trigger secretion of a tumor cell-killing factor that includes tumor necrosis factor-alpha (TNF-A) and to contact the primed monocytes. Tumor cells are contacted with the secreted tumor cell-killing factor.

In one variant of the above method, using monocytes as an exemplary sub-population of effectors that are primable and ultimately primed, monocyte priming is carried out in vivo and provides primed monocytes in addition to any primed monocytes (macrophages) that are present naturally. Here, circulating effector cells such as monocytes present in the patient's peripheral blood are primed by parenteral administration of an amount of IFN-G that is sufficient to prime such monocytes.

A typically useful priming amount of IFN-G for such purposes an amount that provides about 4 to about 1000 units per milliliter of the patient's blood. More preferably, an amount of about 20 to about 200 units per milliliter of patient blood is used. It is noted that different suppliers use somewhat different definitions for units of IFN-G and the above amounts are determined for use of recombinant IFN-G[44] as produced by Amgen, Thousand Oaks, Calif.

The IFN-G is generally present in an aqueous physiologically tolerable carrier as is discussed hereinafter. One or more administrations can be used as desired or needed, depending upon a particular patient's response to the treatment.

After the monocyte priming step, the patient is maintained for a time period sufficient for the primed monocytes (macrophages) to concentrate (migrate to and localize) in the tumor and for primed monocytes (macrophages) that have not concentrated in the tumor to be cleared from the patient's blood stream. This maintenance period typically takes about 5 days (120 hours). The normal lifetime of a monocyte in circulation s between 3 and 4 days.

An effective amount of substantially pure CTF is thereafter administered to the patient to admix with and contact the concentrated, primed monocytes (macrophages), and to trigger the secretion of a tumor-killing factor that includes TNF-A. The substantially pure CTF is typically administered in an aqueous composition of a physiologically tolerable carrier in an amount sufficient to trigger the primed cells. Typically useful triggering amounts are discussed hereinafter.

In another variant of the above method, again using monocytes as exemplary, monocyte priming is carried out in vitro. Again, the primed monocytes (macrophages) utilized are in addition to those that can be present in a tumor.

Here, human leukocytes including monocytes are obtained as by leukophoresis from the patient to be treated or another, compatible human donor. (Leukophoresis provides a cell population that includes PBM and thus, effector cells, and also includes granulocytes.) The obtained monocyte-including leukocytes are primed by admixture and contact with a priming amount of INF-G. An exemplary priming amount of INF-G is about 4 to about 200 U/ml for about $1 \times 10^7$ cells/ml. Contact between the monocyte-containing leukocytes and IFN-G is maintained for a time period of about 36 to about 72 hours, or more preferably for about 48 hours where the priming amount of IFN-G is about 20 to about 100 U/ml.

The in vitro-primed monocyte-containing leukocytes are thereafter introduced into the patient, as by intravenous injection. The patient is maintained, and a triggering amount of substantially pure CTF is administered thereafter as described before to effect the primed monocyte-mediated killing of tumor cells.

In yet another embodiment of this method, the entire method is carried out in vitro. Here, PBM containing effector cells exemplified by monocytes are primed by admixture and contact with a priming amount of IFN-G as described elsewhere herein. The primed monocytes (macrophages) are thereafter admixed and contacted with an aqueous composition containing substantially pure CTF, as is also described elsewhere herein, to trigger the secretion of the tumor cell-killing factor that contains TNF-A. Exogenously supplied tumor cells are admixed and contacted with the triggered monocytes.

For the before-described in vivo methods, the patient's blood stream is preferably assayed prior to carrying out the method to determine whether primed monocytes are present in the circulation. That assay can be carried out by obtaining a monocyte-containing sample to be assayed such as PBM. A triggering amount of an aqueous CTF-containing composition is admixed with the monocyte-containing sample, and triggering of secretion of the TNF-A-containing tumor cell killing factor is assayed as by use of the Act-D-treated WEHI 164 cells as described herein. If circulating primed monocytes are found to be present, the patient is preferably not treated until the primed monocytes are cleared from the patient's blood stream, as described herein.

It is also preferred to assay the patient's monocytes prior to in vivo treatments to determine that that patient's monocytes or other effector cells can be primed and triggered, since a rare patient could have a genetic abnormality that prevents his or her effector cells from becoming primed and triggered. For example, in the mouse system, the C3H/HeJ strain of mice does not respond to LPS. The patient's effector cells can be assayed for priming and triggering with the standard three-stage assay method described herein.

Primed human monocytes (macrophages) are differentiated monocytes, as already noted. Primed human monocytes can be distinguished from unprimed monocytes (macrophages). $5 \times 10^5$ Primed cells per milliliter when contacted with about 1 picogram per milliliter of LPS secrete the tumor cell-killing factor containing TNF-A that kills target cells such as Act D-treated WEHI 164 cells in the lysis assay described herein during a 6 hour time period. Unprimed cells secrete a lesser amount of that factor, and resultantly produce less cytotoxicity of such target tumor cells under similar conditions. The unprimed monocyte requires about one thousand times more LPS to trigger cytotoxicity than does a primed monocyte.

Thus, an assay can be carried out to determine whether cells are primed or unprimed. Here, three aliquots each containing equal numbers of effector cells per milliliter are prepared as described in Section V E, Stage I (Priming). IFN-G at 525 U/ml in 20 ul of medium is admixed with one aliquot (aliquot A) while 20 ul of medium free of IFN-G is added to each of the other aliquots (aliquots B and C). The effector cells of each of the three aliquots are then treated as discussed in that Priming section.

At the end of the 48-hour incubation period, LPS is admixed with aliquots A and B in an amount sufficient to provide an LPS concentration of 1 picogram per milliliter. An amount of LPS sufficient to provide a concentration of 100 nanograms per milliliter is admixed with aliquot C at that time. The admixtures so prepared are maintained in the incubator for a time period of 6 hours, as described in Section V E, Stage II (Triggering).

At the end of that 6 hour time period, equal numbers of target cells are admixed with each of aliquots A, B and C, and those admixtures are maintained as described in Section V E, Stage III (Lysis). Percent Specific Release is then determined for each aliquot.

If the effector cells originally utilized in each of the three aliquots were primed, the Percent Specific Release for each of the three aliquots would be substantially the same. If those effectors were not originally primed, the Percent Specific Release for aliquots A and C would be substantially the same, while that for aliquot B would be substantially less.

It is to be understood that tumor cells can be killed in other than lytic pathways. However, lysis and the $^{51}$Cr-release assay described herein are convenient means by which the death of tumor cells and the presence of suitably primed monocytes can be assayed, particularly in vitro.

An effective, primed monocyte triggering amount of substantially pure CTF varies inter alia with the type of tumor cells to be killed, their number, the size of the tumor (for in vivo lysis), the frequency of administration and the like as is well known in the art. Typically, about 600 to about 60,000 units/kilogram of body weight (U/kg) of substantially pure CTF are administered, with an amount of about 6000 U/kg being a typical dose. When viewed from the point of view of the plasma of a treated patient, it is desirable to administer an amount of substantially pure CTF sufficient to provide about 10 to about 1000 U/ml of plasma, and typically about 100 U/ml.

Exemplary in vitro effective amounts are those enumerated hereinbefore.

Tumors contain suitably primed monocytes (macrophages), as already noted. It is also known that tumors are well vascularized, and that the vascular system in tumors has been shown to be relatively permeable to plasma proteins. Senger et al., (1983) *Science* 219:983; and Dvorak et al. (1984) *Cancer Research* 44:3348.

The existence of a tumor causes monocytes to migrate to the tumor and primed macrophages to concentrate in the tumor as compared to the remainder of the body tissues or fluids where those primed cells are present in minimal numbers. The relatively high permeability of the tumor vascular system causes parenterally administered CTF to concentrate in the tumor where the concentration of primed monocytes (macrophages) is highest. Thus, parenteral administration of CTF to a patient with a tumor concentrates the CTF at the site of the highest concentration of monocytes (macrophages).

Thus, substantially pure CTF can be contacted with the primed monocytes (macrophages) in vivo by parenteral introduction as by injection of a composition containing an effective amount of CTF in an aqueous composition containing a physiologically tolerable carrier into the patient so that the CTF can be carried to the tumor cells by a bodily fluid such as plasma or lymph. Exemplary parenteral introductions into a patient include intramuscular, intraperitoneal, intravenous, intratumoral and the like injections and infusions.

It is reiterated that CTF operates only on activated or primed effector cells such as monocytes (macrophages) as are present within tumors, and are substantially absent from the remainder of the body of a person otherwise free from an inflammatory condition. In addition, macrophages are relatively immobile and are not observed to travel within the body as do their precursor, unprimed monocytes. As a consequence of these facts, a systemic in vivo administration of substantially pure CTF provides localized killing of tumor cells; i.e., killing substantially only at the situs of the tumor.

Analyzing the circumstances of tumor cell killing still further, it is seen that for in vivo methods, the primed monocytes (macrophages) triggered in a patient are substantially only those monocytes (macrophages) primed within the patient's tumor. Furthermore, the tumor cells contacted with the TNF-A-containing tumor-killing factor are the cells of the tumor within which the primed monocytes are triggered.

Where the method is practiced in vitro, human monocytes are preferably primed as described herein, using IFN-G. Similarly, contact between the primed monocytes (macrophages) and CTF, and between target tumor cells such as Act D-treated WEHI 164 cells and TNF-A-containing primed monocyte (macrophage) secretions are preferably maintained as described herein. Target tumor cells are admixed in an in vitro system from an exogenous source within about 10 hours after monocyte (macrophage) triggering has commenced, and the ratio of primed monocytes (macrophages) in the admixture to target tumor cells is about 0.6:1 to about 20:1, and more preferably about 10:1.

The substantially pure CTF of this invention, in glycosylated or unglycosylated forms, can be obtained by freeze drying an appropriate aqueous composition (solution or dispersion).

Aqueous physiologically acceptable carriers are well known in the art. All carriers include sterile, substantially pyrogen-free (e.g. endotoxin-free) water, and thus contain less than 0.01 ng/ml, and preferably less than about 0.001 ng/ml, of endotoxin as measured in the Limulus amoebocyte lysate assay or the USP Pyrogen Test, *The United States Pharmacopeia*, 17th ed., page 863 (1965). Briefly, in accordance with the USP Pyrogen Test, three rabbits are injected intravenously within a two minute time period with a dose of 10 milliliters per kilogram of body weight of an aqueous composition containing a material to be assayed. Body temperatures are thereafter measured at 1,2 and 3 hours after the injection. If no rabbit shows an individual rise in temperature of 0.6° C. or more above its control temperature, and if the sum of the three temperature rises does not exceed 1.4° C., the material examined meets the requirements for the absence of (freedom from) pyrogens.

Exemplary of useful carriers are aqueous solutions that contain no materials in addition to CTF and water, or contain a buffer such as sodium phosphate at physiological pH value, physiological saline or both, as in phosphate-buffered saline. Still further, aqueous carriers can contain more than one buffer salt, as well as salts such as sodium and potassium chlorides, sugars such as mannose, mannitol and dextrose, proteins such as serum albumin and other solutes. These latter carriers are exemplified by Ringer's injection, dextrose injection, dextrose and sodium chloride injection and lactated Ringer's injection.

An aqueous CTF-containing composition useful herein can be administered once in a method of this invention, or more usually, a plurality of times during a treatment regimen of weeks to several months.

Substantially pure CTF can be packaged in dry form for dissolution prior to use as a composition of this invention or as a composition itself. When so packaged, the CTF is in unit dosage form in that it is in physically discrete units suitable as unitary dosages for administration, each containing a predetermined quantity of the lymphokine calculated to produce the desired effect. Examples of suitable unit dosage forms include powder packets, granules, ampules, vials and the like.

IV. Results

A. Basic Assay System

For assay of monocyte-mediated cellular cytotoxicity, the Actinomycin (Act) D-treated WEHI 164 murine fibrosarcoma cell $^{51}$Cr release assay previously described and confirmed as specific for human monocyte-mediated cellular cytotoxicity [Ziegler-Heitbrock et al., (1984) *J. Natl. Cancer Inst.* 72:23; and Colotta et al., (1984) *J. Immunol.* 132:936] was adopted and modified for use in a 6 hour assay. The resistance of this target cell line to injury mediated by natural killer (NK) cells, polymorphonuclear neutraphils (PMN) and human T lymphocytes has been demonstrated.

PBM isolated from healthy, normal volunteers (e.g. those free of known diseases, inflammatory conditions and tumors) under scrupulous endotoxin-free conditions were found to reproducibly exhibit little if any spontaneous cytotoxic effector function against this target, contrary to the implications of the originally reported studies, above However, small amounts of LPS from *E. coli* 0111:B4 rapidly induced cellular cytotoxic function (see for example FIG. 1, Panel B).

Since endotoxin is a physiologically irrelevant signal in the normal individual and should not be present in the concentrations needed to induce the observed monocyte-dependent cellular cytotoxicity in typical immunologically mediated lesions, the assay was modified to a prolonged, three-stage format (FIG. 1, Panel A) to search for a novel lymphokine that would exert the same biological effect on monocytes, namely, serve as a "second signal" or trigger to induce cellular cytotoxicity.

One-way mixed allogeneic leukocyte reactions (MLR) were used to generate lymphokine-rich media for the initial search for a triggering lymphokine. Lymphokine-containing medium supernatants (LK-SN) were generated by coculture of normal human effector cell-containing PBM with irradiated Daudi B lymphoblast cells at a 1:3 to a 1:5 ratio for 18–24 hours. As a control supernatant (CO-SN), PBM and the irradiated Daudi cells were cultured separately, and their supernatant media were subsequently mixed at a 1:3 to 1:5 (v/v) ratio.

The preparations of LK-SN contained variable amounts of IFN-G, IL-2 and monocyte procoagulant-inducing factor (MPIF) [Gregory et al., (1984) *Fed. Proc.* 43:1748]. Monocyte cytotoxicity was usually lacking or marginal in PBM admixed and maintained (incubated) with LK-SN for a time period of 6 hours.

Similarly, recombinant IFN-G (rIFN-G) from 0.1–10,000 U/ml completely and reproducibly failed to induce monocyte-mediated cellular cytotoxicity in the same 6 hour time period (See, for example FIG. 3B). Because several studies indicated that IFN-G, functioning as "MAF-I", required 2–3 days to activate monocytes [Nakagawara et al., (1982) *J. Clin. Invest.* 70:1042; Gately et al., (1983) *J. Immunol.* 131:2583; Murray et al., (1983) *J. Clin. Invest.* 72:1506; and Herrmann et al., (1985) *J. Exp. Med.* 162:1111], PBM were cultured and maintained (incubated) for 48–96 hours in the three-stage assay with or without various agents. Representative results from comprehensive screening studies are shown in FIG. 1.

The principal finding, reproducibly observed using PBM from eight donors, is that LK-SN elicited vigorous cytotoxicity when admixed and maintained in contact with IFN-G-primed cells (FIG. 1, Panel C). When PBM in various concentrations were cultured in medium alone for 48 hours in the absence of a first signal as provided by IFN-G, the addition of LK-SN as a second signal 6 hours prior to addition of target cells did not elicit a significant cytotoxic response.

However, when the PBM had been cultured in the presence of IFN-G at 150 U/ml for 48 as the first signal, the addition of LK-SN as a second signal induced vigorous cytotoxic activity against the Act D-treated WEHI 164 target cells. If no exogenous IFN-G were added, and PBM were cultured for 48 hours with LK-SN (containing 50–300 U/ml of endogenous IFN-G), monocyte cytotoxicity was typically observed.

In contrast, control medium supernatants (CO-SN) failed to induce significant cytotoxicity under any condition (FIG. 1, Panel D). These effects were not solely attributable to the IFN-G present in the preparations of LK-SN serving as both first and second signals since addition of IFN-G alone failed to elicit a cytotoxic response (FIG. 1, Panel B).

Lymphokine-rich media produced by nylon-wool enriched human T cells were also examined as a source of the second signal lymphokine. After a 3 hour pulse with optimal concentrations of phorbol myristate acetate (PMA) and calcium ionophore A23187 (CaI) (PMA/CaI-SN) and subsequent cultivation for 48 hours, media were produced that contained less than 1 U/ml IFN-G (FIG. 1, Panel E). The concentration of lymphokine(s) responsible for induction of cytotoxicity following this PMA/CaI-SN induction protocol sequence was considerably greater than in LK-SN.

Priming of effector cell-containing human PBM with IFN-G for 48 hours significantly enhanced the effector function when an aqueous composition of substantially pure CTF obtained from a Sephadex G-100sf fraction at about 55 kd of PMA/CaI-SN was admixed and used as the second signal. There was some cytotoxicity without priming that is under further investigation, and is thought to have been due to an inadvertently present contaminant.

These studies indicate first that PBM lack spontaneous cytotoxicity against Act D-treated WEHI 164 cells. Second, endotoxin is one inducer of this latent activity. Third, IFN-G is insufficient alone to induce this activity. Fourth, an inductive lymphokine; i.e., CTF, is released into the medium of immunologically (LK-SN) as well as chemically stimulated (PMA/CaI-SN) PBM and T lymphocytes.

IFN-G (MAF-I) thus serves as the priming lymphokine and CTF serves as the triggering lymphokine for induction of vigorous cytotoxicity. This interpretation is supported by the results of the studies that follow.

B. Effector Cell Specificity

Act D-treated WEHI 164 cells are convenient targets for monocyte cytotoxicity because they are known to be resistant to NK, T lymphocyte and PMN killing. [Ziegler-Heitbrock et al., (1984) *J. Natl. Cancer Inst.* 72:23; and Colotta et al., (1984) *J. Immunol.* 132:936 ]. Unfractionated PBM were used as effectors rather than purified monocytes because the risk of endotoxin (e.g., LPS) contamination that is associated with cellular fractionation and the possibility of multiple interactive cell subsets. However, since exogenous lymphokines were admixed with the PBM used as effectors, other types of lymphokine-activated killer cells may have been induced [Grimm et al., (1982) *J. Exp. Med.* 155:1823; Warren, (1984) *J. Immunol.* 132:2888; Svedersky et al., (1985) *J. Immunol.* 134:1604; and Yang et al., (1985) *J. Immunol.* 134:3912]. Thus, the specificity of this assay for monocyte-mediated killing was reassessed.

A monoclonal antibody (TNFD) that specifically neutralizes the cytotoxicity of TNF-A in the L929 cell assay for TNF-A [Armstrong et al., (1985) *J. Natl. Canc. Inst.* 74:1] abolished the cytotoxicity induced by CTF in IFN-G-primed PBM as measured in the 6 hour $^{51}$Cr release assay using Act D-treated WEHI 164 cells (FIG. 2, Panel A). TNF-A alone, in the absence of effector cells, elicited similar degrees of cytotoxicity in the presence of IFN-G (FIG. 2, Panel B) to those induced by CTF.

Thus, TNF-A is necessary to mediate the cytotoxicity induced in PBM by CTF in conjunction with IFN-G. The fact that TNF-A has been established as a monocyte/macrophage product [Old, (1985) *Science* 230:630] provides further evidence that the Act D-treated WEHI 164 cell assay is specific for monocyte-mediated cytotoxicity. Consequently, the IFN-G-primed and CTF-stimulated effector cells are defined at least as monocytes and/or macrophages. This definition does not, however, preclude the involvement of other cells.

C. Time and Dose Requirements for INF-G Priming

It was consistently observed that PBM pretreated with IFN-G were more sensitive (or "primed") to the cytotoxicity-inducing (or "triggering") effect of CTF-containing compositions. IFN-G priming was required to detect the lower levels of CTF present in LK-SN produced by allogeneically stimulating PBM with irradiated Daudi cells that themselves serve as stimulators yet do not themselves produce a cytotoxin or CTF.

When constant amounts of LK-SN were admixed in the triggering stage of the assay to effector cell-containing PBM primed with 150 U/ml IFN-G for varying times in culture, more than 24 hours were required for the priming effect to be evident (FIG. 3, Panel A). Using an extensive checkerboard analysis of: (a) IFN-G dose and (b) duration of stage I priming time of admixture, effective priming for responsiveness to the triggering signal was evident at 36 hours, complete at 48 hours, and was neither accelerated nor enhanced by higher doses of IFN-G. Priming did not diminish when IFN-G was present for up to 96 hours in culture.

As an exception, IFN-G admixed after the triggering LK-SN, and immediately prior to admixture of the target cells, variably and mildly enhanced the degree of cytotoxicity. This was an inconsistent finding, and was observed only when the LK-SN preparation used as the second signal to trigger PBM also contained a cytotoxic factor, possibly TNF-A or lymphotoxin (TNF-B). Thus, for all preparations of CTF it has been necessary to analyze for the presence of direct cytotoxin, and either use only preparations substantially free of direct cytotoxin or fractionate the preparations as on Sephadex G-100sf to recover enriched, substantially pure CTF that is substantially free of direct cytotoxin.

The effect of IFN-G was not merely to synergize cytotoxically with the induced TNF-A. Whereas such synergy can account for some of the apparent enhancement of cytotoxicity that IFN-G produces [Williamson et al., (1983) *Proc. Nat. Acad. Sci. U.S.A.* 80:5397; and Stone-Wolff et al., (1984) *J. Exp. Med.* 159:828], it does not explain the time requirement needed for IFN-G to prime for maximum effect. This occurs at 48 hours, by which time IFN-G should be relatively depleted from the medium through receptor-mediated consumption by cells present in the PBM. In support of this interpretation, IFN-G has been reported to require a similar time period (48-72 hours) in order to induce other macrophage-activating effects. Nakagawara et al., (1982) *J. Clin. Invest.* 70:1042; Gately et al., (1983) *J. Immunol.* 131:2583; Murray et al., (1983) *J. Clin. Invest.* 72:1506; and Herrmann et al., (1985) *J. Exp. Med.* 162:1111.

To determine the dose of IFN-G required for priming, PBM were cultured for 48 hours with varying doses of IFN-G, and then triggered with a constant effective amount of CTF-containing LK-SN for 6 hours (FIG. 3, Panel B). The threshold dose for the IFN-G primary effect varied from 4 to 20 U/ml and priming was maximal at 20-100 U/ml. Natural IFN-G (nIFN-G) and recombinant IFN-G (rIFN-G) did not significantly differ in their abilities to prime PBM.

As is shown in FIG. 3, Panel B, IFN-G in dosages of up to 5,000 U/ml failed to directly induce cytotoxicity in the absence of subsequent second signal lymphokine; i.e. CTF, triggering. This is about 100-fold greater than the concentration of IFN-G found in any of the LK-SN preparations.

In a checkerboard analysis of IFN-G priming, doses greater than the maximal dose at 48 hours did not appreciably accelerate or enhance the priming effect. Consequently, IFN-G exposure at 150 U/ml for 48 hours was used to prime the effector cells in all further studies of CTF requirements.

D. Time and Dose Requirements for CTF Triggering

The admixture of exogenous sources of CTF to IFN-G-primed effector cell-containing PBM and maintenance of the resulting contact rapidly induced vigorous cytotoxic activity measured in the final 6-hour lytic phase of the assay (FIG. 4). The interval of triggering by LK-SN or the substantially pure CTF of the 55 kd fraction of PMA/CaI-SN was shortened from 6 to zero hours. In a series of five studies, triggering of monocyte-induced cytotoxicity by LK-SN increased over time to a maximum after 6 hours. Consequently, 6 hours of CTF exposure was used as the triggering period prior to the 6 hour cytotoxic effector period for systematic analysis.

In order to examine the quantitative requirements for CTF, IFN-G-primed PBM effectors were admixed with varying concentrations of LK-SN or the substantially pure CTF of the 55 kd fraction of PMA/CaI-SN in the 6 hour triggering phase. The degree of cytotoxicity produced had a sigmoidal relationship to the dose of CTF added, and reached a plateau of maximum activity (FIG. 5).

One unit of CTF was defined under these conditions as the amount of CTF that in 6 hours induced one-half-maximal cytotoxicity in PBM primed with IFN-G (150 U/ml for 48 hours), using an effector to target cell (E:T) ratio of 50:1 against $10^4$ Act D-treated WEHI 164 target cells. In these examples, the LK-SN preparation typically used contained 44 CTF U/ml and the usually used PMA/CaI-SN contained 100 CTF U/ml. C-10/MJ2 cell serum-free medium [discussed in Section IV(H)], after 4 hours of secretion, provides about 2000 U/ml or 40,000 U/mg protein, which, on further purification provides an activity of about 300,000 U/mg total protein.

E. Production of CTF by Cloned Human T Lymphocytes

Alloantigen-responsive normal human T lymphocyte clones were generated in vitro by stimulation with irradiated Daudi cells and cloning by established methods. Gregory et al., (1985) *J. Clin. Invest.* 76:2440. Fifty-one normal T cell clones were selected and analyzed for the capacity to produce CTF in response to allogeneic stimulation. T cell clones were incubated with or without irradiated Daudi cells at optimal ratios (2-6 Daudi cells per T cell depending on clone) for intervals from 4 to 72 hours. The media were harvested and analyzed for CTF using IFN-G-primed PBM as effectors.

As is shown in FIG. 6 for two representative clones, CTF was not observed as a constitutive T cell product in vitro. Optimal allogeneic stimulation resulted in CTF production by T helper clone 62, which had the T3+T4+T8−M1− phenotype. In contrast, clone 25 is of the same phenotype and did not produce CTF, although it did produce IL-2. Normal T cell clones of other than T3+T4+T8−M1− phenotype were not observed to secrete CTF.

These results clearly assign CTF biosynthesis to normal T helper cells and implies the need for T receptor engagement in the control of biosynthesis; but it does not entirely exclude the possibility of production of CTF by other as yet unidentified cells. In addition, the helper T phenotype appears to be a necessary but not sufficient criterion for determining those T cells that are capable of secreting CTF.

F. Physicochemcial Characterization of CTF

The most revealing evidence that CTF is a single distinct molecular entity rather than the combined effect of a mixture of molecules is provided by size fractionation by molecular exclusion chromatography on Sephadex G-100 superfine (sf). Most CTF activity reproducibly eluted as a discrete peak with an apparent relative mass ($M_r$) of about 55 kd under non-dissociating conditions (FIG. 7). For some preparations, one or two additional peaks of marginally detectable activity have been observed with apparent $M_r$ of 14 kd and greater than 150 kd. Those results suggest that 55 kd CTF may be an aggregate that can exist in the lower and higher molecular weight forms, or that one or two different additional molecules are also secreted from T cells that are capable of inducing cytotoxicity of the target tumor cells by primed PBM.

CTF activity has been recovered well separated from IL-2, and the cytotoxin occasionally found in LK-SN preparations. The 55 kd CTF-positive peak lacked activity in a migration inhibitory factor (MIF) assay, and was negative for colony stimulating factor-1 (CSF-1) by radioimmunoassay, and granulocyte-macrophage colony stimulating factor (GM-CSF) by bioassay.

Although the 55 kd CTF-positive peak co-elutes with IFN-G when the latter is present in LK-SN or PMA/CaI-SN, the minor 150 kd and 14 kd peaks contain no detectable IFN-G. Furthermore, CTF activity is not removed from LK-SN preparations of CTF by passage through an anti-IFN-G immunoaffinity column, although IFN-G was reduced from 55 to less than 1 U/ml.

In addition, while PMA/CaI-SN prepared from nylon wool-purified normal human T cells lacked IFN-G, IL-2, and the cytotoxin, it was found to contain the major about 55 kd peak and a minor greater than 150 kd CTF peak. The 55 kd CTF from PMA/CaI-SN lacked direct cytotoxic activity against L929 in the assay for TNF-A or TNF-B. Armstrong et al., (1985) *J. Natl. Conc. Inst.* 74:1. Thus, CTF is distinct from IFN-G, IL-2, TNF-A, TNF-B or other direct cytotoxin, as well as MIF, CSF-1 and GM-CSF.

G. Other Well-Characterized Cytokines Do Not Function as a CTF

The ability of various well-characterized cytokines to function as a CTF in the standard three-stage assay using IFN-G primed effectors in PBM has also been examined. The results of this examination are shown in Table I, below. A summary of the distinctions between CTF and the cytokines of Table I is presented in Table II that follows Table 1.

TABLE I

LACK OF ACTIVITY OF WELL-CHARACTERIZED CYTOKINES IN THE BASIC CTF ASSAY[1]

| CYTOKINE | CONCENTRATION[2] | INDUCED CYTOTOXICITY[3] |
|---|---|---|
| Comparison 1 | | |
| CTF (LK-SN 55kd G-100sf fraction) | N.D.[4] | 31.7 ± 18.7 |
| nIFN-G | 10 U/ml | 0.5 ± 6.1 |
|  | 100 | 6.4 ± 3.2 |
|  | 1,000 | 0.0 ± 7.9 |
|  | 10,000 | 2.0 ± 3.1 |
| rIFN-G | 10 U/ml | −1.6 ± 4.7 |
|  | 100 | 4.2 ± 4.2 |
|  | 1,000 | 2.7 ± 4.7 |
|  | 10,000 | −2.1 ± 5.9 |
| nIL-2 (contaminated with IL-1 and positive for endotoxin by Limulus assay) | 1.6 U/ml | 4.2 ± 4.2 |
|  | 6.25 | −4.0 ± 5.1 |
|  | 25 | 18.6 ± 2/9 |
| Comparison 2 | | |
| CTF (LK-SN) | 111 U/ml | 64.7 ± 7.4 |
| nIL-1 (beta) | 1.6 U/ml | 10.9 ± 6.8 |
|  | 3.1 | 16.9 ± 5.6 |
|  | 6.3 | 11.8 ± 2.2 |
|  | 12.5 | 19.9 ± 1.6 |
|  | 25 | 16.2 ± 3.4 |
| rGM-CSF | 7.8 ng/ml | 32.3 ± 11.5 |
|  | 31 | 22.8 ± 6.6 |
|  | 125 | 28.3 ± 14.5 |
|  | 500 | 30.8 ± 8.4 |
| rIL-2 | 5 U/ml | −9.9 ± 4.5 |
|  | 50 | −1.4 ± 3.9 |
|  | 500 | 19.0 ± 3.0 |
| Comparison 3 | | |
| CTF (LK-SN 55 kd G-100sf fraction) | N.D. | 30.0 ± 4.0 |
| CTF (PMA/CaI-SN) | 57 U/ml | 63.2 ± 3.6 |
| nIL-1 (beta) | 0.5 U/ml | −2.1 ± 1.2 |
|  | 1 | −2.8 ± 0.9 |
|  | 5 | 0.8 ± 4.1 |
|  | 10 | 6.1 ± 2.2 |
|  | 50 | 7.2 ± 5.0 |
| Comparison 4 | | |
| CTF (LK-SN) | 44 U/ml | 30.4 ± 6.6 |
| rIL-1 (alpha) | 1 U/ml | 10.1 ± 2.0 |
|  | 3 | 10.3 ± 1.6 |
|  | 10 | 10.3 ± 3.5 |
|  | 30 | 12.9 ± 5.5 |
| rIL-1 (beta) | 1 U/ml | 8.7 ± 1.3 |
|  | 3 | 10.5 ± 0.3 |
|  | 10 | 7.7 ± 4.0 |
|  | 30 | 19.5 ± 7.9 |
| Comparison 5 | | |
| CTF (LK-SN) | N.D. | 28.3 ± 3.3 |
| rCSF-1 | 1 U/ml | 13.5 ± 2.5 |
|  | 10 | 9.5 ± 3.9 |
|  | 100 | 11.8 ± 1.9 |
|  | 1,000 | 32.1 ± 4.7 |

[1]Cytotoxicity in the "basic assay" was determined as described in the MATERIALS AND METHODS section V(E). Cytokines utilized for comparisons were obtained from sources listed in section V.
[2]Concentrations are given in units per milliliter (U/ml) or nanograms per milliliter (ng/ml).
[3]Cytotoxicity is reported in percent specific release, as defined herein, ± the standard deviation.
[4]N.D. = not determined.

TABLE II

SUMMARY OF DISTINCTIONS BETWEEN CTF AND OTHER WELL-CHARACTERIZED CYTOKINES

| CYTOKINE | DIFFERENCES FROM CTF |
|---|---|
| IFN-G | (a) lacks ability to induce cytotoxicity even at 100 times more than its level in LK-SN; |
|  | (b) can be removed from LK-SN by a monoclonal antibody immunoaffinity |

TABLE II-continued
SUMMARY OF DISTINCTIONS BETWEEN CTF AND OTHER WELL-CHARACTERIZED CYTOKINES

| CYTOKINE | | DIFFERENCES FROM CTF |
|---|---|---|
| | | column without loss of CTF activity; and |
| | (c) | is absent from PMA/CaI-SN, which contains CTF. |
| IL-2 | (a) | totally inactive in inducing cytotoxicity at low levels found in LK-SN; |
| | (b) | elutes separately from CTF on Sephadex G-100sf; and |
| | (c) | is absent from PMA/CaI-SN, which contains CTF. |
| IL-1 | (a) | lacks ability to induce cytotoxicity at levels more than 10 times higher than its level in LK-SN. |
| GM-CSF | (a) | lacks ability to induce cytotoxicity at levels much greater than its level in LK-SN; and |
| | (b) | is absent from LK-SN and from 55 kd Sephadex G-100sf fractions containing CTF. |
| TNF-A | (a) | is absent from 55 kd Sephadex G-100sf fractions containing CTF; and |
| | (b) | is absent from PMA/CaI-SN, which contains CTF. |
| TNF-B | (a) | is absent from 55 kd Sephadex G-100sf fractions containing CTF. |
| CSF-1 | (a) | lacks CTF activity; and |
| | (b) | is absent from 55 kd Sephadex G-100sf fractions containing CTF. |
| MIF | (a) | is absent from 55 kd Sephadex G-100sf fractions containing CTF. |

Examination of the above Tables shows that IFN-G, IL-2, IL-1-alpha and -beta, GM-CSF, CSF-1, TNF-A and TNF-B did not substitute for or function as CTF at the doses in which they are present in any of the CTF-positive preparations.

It is thus concluded that none of the cytokines examined is responsible for the CTF activity observed in any CTF preparations made during this study. This conclusion is consistent with an independent molecular identity of CTF.

H. Production of CTF by Transformed T Cells

The work described before in Section IV(E) related to CTF production in normal human T helper cells; i.e., T helper cells from healthy humans. The work described in this section relates to the production of CTF from T cells transformed by HTLV-I.

The particular HTLV-1-transformed cell line used is denominated C10/MJ2, and was obtained from the National Institutes of Health, Bethesda, Md., at which place it is deposited and available to qualified workers. This cell line was developed by Dr. Robert Gallo and his coworkers, and is described in Popovic et al., (1983) *Science* 219:856.

In addition to the C10/MJ2 cell line, other transformed or malignant T cell lines are also capable of secreting CTF. Exemplary of such cell lines are: GM 3104A, a lymphoblast cell line available from the National Institutes of General Medical Sciences Human Genetic Mutant Cell Repository; and HuT 102 (ATCC TIB 162), reported to be originally obtained from peripheral blood of a patient with mycosis fungoides.

The C10/MJ2 cells used herein grow at an optimal concentration of about $0.5-2 \times 10^7$ cells/ml in a protein-free medium. The medium used was the "medium" described in Section V(A) from which FBS was omitted.

These C10/MJ2 cells secrete CTF into the medium in the presence of the glycosylation inhibitor tunicamycin present at 1 microgram/ml and higher for time periods of 4 to 8 hours. In addition, contrary to normal helper T cells, C10/MJ2 cells are constitutive CTF producers in that they secrete impure CTF substantially continuously without exogenous stimulation as by PMA/CaI or irradiated Daudi cells.

Substantially pure CTF was obtained from the culture of C10/MJ2 cells as follows. The cells were grown at a concentration of $0.5-4 \times 10^7$ cells/ml in the protein-free medium for a time period of 3–8 hours. The culture medium supernatant was separated from the cells by usually used low speed centrifugation. The supernatant from that centrifugation was thereafter centrifuged at 100,000xg for a time period of 1.5 hours at 4° C. to remove cell debris and HTLV-I particles. The clear fluid was then passed through a 25 nanometer pore filter to remove residual virus and cell debris. The activity of the CTF so prepared was about 40,000 units per milligram of protein.

That CTF preparation was dialyzed against PBS at pH 7.2, concentrated by ultrafiltration using an Amicon ultrafiltration device and a YM-10 filter, and then fractionated by gel exclusion chromatography using Sephadex G-100sf. The major substantially pure CTF protein having an $M_r$ of about 55 kd was recovered as were the two minor substantially pure proteins having CTF activity and relative masses of about 14 kd and greater than about 150 kd, as discussed before. The activity of the substantially purified CTF having an $M_r$ of about 55 kd was about 300,000 units/milligram of total protein.

V. MATERIALS AND METHODS

A. Culture Materials

All reagents were demonstrated to be substantially endotoxin-free (less than 0.01 ng/ml) and were prepared in endotoxin-free water (Travenol Laboratories, Deerfield, Ill.). Ficoll 400 (Sigma Chemical Co., St. Louis, Mo.) was dissolved in that water and added to Hypaque (50% diatrizolate, Winthrop Laboratories, Menlo Park, Calif.) to a density of 1.074 grams per milliliter (g/ml). Selected lots of RPMI 1640 (obtained from Whittaker M.A. Biologicals, Walkersville, Md. or GIBCO, Grand Island, N.Y.) that were found to be endotoxin-free were used in all studies. HEPES [4-(2-hydroxyethyl)-1-piperazineethanesulfonic acid; CALBIOCHEM Biochemicals, Behring Diagnostics, La Jolla, Calif.] was dissolved in pyrogen-free water to a concentration of 1.5 molar (M), and adjusted with NaOH so that at 25 millimolar (mM) in RPMI 1640 the pH value was 7.30. "Medium" was RPMI 1640 that contained 25 mM HEPES, as well as 50 micrograms per milliliter (ug/ml) gentamicin (Schering Corp., Kenilworth, N.J.), and was supplemented with 10 percent fetal bovine serum (FBS) from selected substantially endotoxin-free lots (obtained from Irvine Scientific, Santa Ana, Calif.; K.C. Biologicals, Lenexa, Kans.; and Sterile Systems, Inc., Logan, Utah).

Phosphate-buffered saline (PBS) [NaCl 8 grams per liter (g/l), KCl 0.2 g/l, $NaH_2PO_4$ 0.2 g/l, $Na_2HPO_4\cdot 7H_2O$ 2.16 g/l] was made with the pyrogen-free water and had a pH value of 7.20. Trypsin-EDTA was from Irvine Scientific.

96-Well U-bottom tissue culture plates (#3799) and 75 ml flasks were from Costar (Cambridge, Mass.). 50 Milliliter polypropylene tubes were from Corning Glass Works (Corning, N.Y.).

B. Chemicals

Heparin 500 units per milliliter (U/ml) (Elkins-Sinn, Inc., Cherry Hill, N.J.); actinomycin D (Act D) and phenol-extracted lipopolysaccharide from *Escherichia coli* 0111:B4 (LPS) were from CALBIOCHEM Biochemicals. $^{51}$Cr as sodium chromate and Aquasol were from New England Nuclear, Boston, Mass. YM-10 Diaflo ultrafilters were from Amicon Corp., Danvers, Mass. Sephadex G-100sf was from Pharmacia Fine Chemicals, Piscataway, N.J. IMRX Interferon-gamma RIA was from CENTOCOR, Malvern, Pa.

C. Cell Preparation

Peripheral blood monocytes (PBM) were prepared by collecting venous blood from healthy (normal) volunteers (free from known tumors or other monocyte-priming conditions) into heparin to give 5 U/ml final. The blood was centrifuged at 120Xg for 25 minutes, and the platelet-rich plasma was removed. The blood was restored to its original volume with medium and a second platelet-depleting centrifugation was performed. Following this, effector cell-containing PBM were isolated using Ficoll-Hypaque, and were washed 3 times in medium without FBS. These cells were more than 98 percent viable by trypan blue exclusion and consisted of 15–20 percent monocytes as determined by esterase staining. In some instances, monocyte-depleted T cells were purified on nylon wool columns as described in Falkoff et al., (1982) *J. Immunol. Methods* 50:39. Unless otherwise stated as above, all media were supplemented with 10 percent FBS.

D. Target Cell Labeling.

Mycoplasma-free WEHI 164 murine fibrosarcoma cells (a gift of Dr. Ronald Herberman, National Cancer Institute) were cultured in endotoxin-free RPMI 1640 medium supplemented with selected endotoxin-free 10 percent FBS at 37° C. in an atmosphere containing 5 percent $CO_2$ in air. Target cells were passaged using trypsin-EDTA two days before a study. On the day of the study, cells were detached from the culture vessel using trypsin-EDTA with gentle shaking. Prior to labeling, $5 \times 10^6$ WEHI 164 cells were pretreated with 1 ug/ml Act D in 30 ml of medium for 3 hours in a 50 ml tube as described in Falkoff et al., (1982) *J. Immunol. Methods* 50:39, then pelleted at 120Xg for 5 minutes, and all but 0.5 ml of medium was removed.

200 MicroCuries (uCi) of $^{51}$Cr in normal saline (200–900 ci/g) were then added. The tube was gently mixed and was returned to the incubator. After 1 hour, the labeled cells were washed by 5 cycles of suspension in PBS followed by pelleting at 120Xg for 5 minutes. Specific activity was 2.7 uCi/$10^6$ cells.

E. Cytotoxicity testing

The design of the prolonged three-stage cytotoxicity assay was adapted from previously described methods [Ziegler-Heitbrock et al., (1984) *J. Natl. Cancer Inst.* 72:23; and Colotta et al., (1984) *J. Immunol.* 132:936], and is shown schematically in FIG. 1, Panel A.

Stage I (Priming): PBM were serially diluted in medium at from $2 \times 10^7$/ml to $6.25 \times 10^5$ cells/ml, and 50 microliters (ul) were loaded into the round-bottomed microwells of a 96-well plate. Blank wells were loaded with 50 ul medium without PBM, and "total lysis" wells were loaded with 50 ul of 1 percent sodium dodecyl sulfate (SDS) in water.

IFN-G was incorporated into this stage by adding 20 ul of medium containing a concentration of IFN-G that yielded the final concentration indicated (e.g., 20 ul of medium containing 525 U/ml IFN-G were added to 50 ul of PBM to yield 70 ul of PBM with 150 U/ul of IFN-G). Alternatively, when the IFN-G dose was kept constant, 150 U/ug were added directly to PBM prior to loading 50 ul of cells in medium into the microwells. Plates were centrifuged for 3 minutes at 40Xg, and then incubated at 37 degrees C. in 5 percent $CO_2$ in air for a time period of 48 hours.

Unless otherwise stated, all studies used recombinant IFN-G (rIFN-G$^{4A}$; Amgen) for priming. In other studies, natural IFN-G (nIFN-G) acted in a substantially identical manner.

Stage II (Triggering): At the times indicated, 50–100 ul of lymphokine-containing media or cytokine preparations were added to the wells containing PBM, and the plates were returned to the incubator for a 6-hour incubation period. The final concentration of a triggering agent was calculated using the volume present during this stage of the assay.

Stage III (Lysis): The lytic stage was initiated by admixing 50 ul of the $^{51}$Cr-labeled target cells ($2 \times 10^5$/ml in medium) to each well. After centrifugation of the plates at 40Xg for 3 minutes and further culturing and maintenance (incubation) for 6 hours, one-half of the supernatant medium from each well was removed and counted in 2 ml Aquasol for 1 minute in the tritium channel of a scintillation counter. In a typical study using serum-free medium, background release was less than $2 \times 10^3$ counts per minute (CPM) and total release was about $20 \times 10^3$ CPM.

Results are expressed as percent specific release, defined as:

$$\% \text{ Specific Release} = \left( \frac{CPM_{study} - CPM_{background}}{CPM_{total} - CPM_{background}} \right) \times 100\%$$

where $CPM_{study}$ are the counts from the well in question; $CPM_{background}$ are the average counts from the wells without PBM, and $CPM_{total}$ are the average counts from the wells that contained SDS (which lysed the target cells). Generally, the "blank" wells used to establish $CPM_{background}$ contained all the components (IFN-G and/or lymphokine) used in the study wells, except for the PBM effectors. Occasionally, lymphokine-containing supernatant medium (LK-SN) also contained a 70 kd cytotoxin, and in these circumstances the $CPM_{background}$ included the counts released directly by this cytotoxin (never more than 15 percent of the total counts). Purified cytokines, including IL-1 alpha and beta, had no direct cytotoxicity against this target. For assaying of chromatography fractions, "blank" wells were set up for each fraction to control for the minor fluctuations of $CPM_{background}$ produced. The assay could also be conducted without FBS with similar results.

All conditions were set up in triplicate or quadruplicate, and replicates were usually with 10 percent of each other. Results are presented as the mean±one standard deviation.

F. Lymphokines, Cytokines, and Antibodies

Natural human IFN-G (nIFN-G) ($0.83 \times 10^6$ U/ml) was from Interferon Sciences, (New Brunswick, N.J.). Recombinant human IFN-G (rIFN-G$^{4A}$) ($1.6 \times 10^7$ U/mg) was from Amgen (Thousand Oaks, Calif.). Natural interleukin-2 (IL-2) (nIL-2) was from Electronucleonics, Inc. (Silver Springs, Md.), and was found to contain endotoxin. Recombinant IL-2 (rIL-2) (98 percent pure by HPLC) and recombinant CSF-1 (rCSF-1) were gifts of Dr. Peter Ralph, Cetus Corp. (Emeryville, Calif.). Radioimmunoassay (RIA) of CSF-1 was kindly performed by Dr. Ralph. Natural interleukin (IL-1) (beta) was obtained from Genzyme Corp. (Boston, Mass.) or from Cistron Technology (Pinebrook, N.J.). Recombinant IL-1 (rIL-1) alpha and beta were obtained from Genzyme. Recombinant granulocyte-monocyte colony stimulating factor (rGM-CSF) was a gift of Dr. Steven Clark, Genetics Institute (Cambridge, Mass.). Recombinant tumor necrosis factor-alpha (TNF-A) (lot 3056-63) ($5.0 \times 10^7$ U/mg) and murine monclonal anti-TNF-A (TNFD) (neutralizing 2,700 units of TNF-A/ug) were gifts from Genentech, Inc. (South San Francisco, Calif.). The MIF assay was kindly performed by Dr. Heinz Remold of Brigham and Women's Hospital, (Boston, Mass.).

Lymphokine-containing supernatant medium (LK-SN) was prepared by coculturing human PBM ($3 \times 10^6$/ml medium) with irradiated Daudi B cells ($3 \times 10^6$/ml) for 18–24 hours at a 3:1 or 5:1 (PBM:Daudi) ratio. To prepare control supernatant medium (CO-SN), PBM and irradiated Daudi cells were cultured separately, and their supernatant media were mixed subsequently in the same ratio.

LK-SN contained 15–100 U/ml IFN-G measured by RIA (CENTOCOR, Malvern, Pa.); 2–5 U/ml lymphotoxin (kindly assayed against L929 cells by Drs. G. A. Granger and R. S. Yamamoto, University of California, Irvine, Calif.); 5–28 U/ml IL-2 measured using thymidine uptake by an IL-2 dependent murine T cell line; monocyte procoagulant inducing factor (MPIF) as assayed by its ability to induce tissue factor expression in human monocytes (Gregory et al., (1984) *Fed. Proc.* 43:1748.); and occasionally a 70 kd cytotoxin that was directly cytotoxic to the target cells. CO-SN contained none of these activities. In order to remove IFN-G from LK-SN, 4 ml of supernatant were passed through a $0.5 \times 8.5$ cm column of anti-human IFN-Gmurine monoclonal antibody linked to Affi-Gel 10 (supplied by Dr. Robert Schreiber, Scripps Clinic and Research Foundation, La Jolla, Calif.) at a flow rate of 3 ml/hour at 4° C.

Phorbol myristate acetate (12-O-tetradecanoylphorbol 13-acetate; PMA; Sigma) and calcium ionophone A23187 (calimycin; CaI;Sigma) containing supernatant medium (PMA/CaI-SN) was prepared using nylon wool nonadherent cells isolated from PBM. These cells were suspended at $2 \times 10^6$/ml in medium containing 10 nanograms per milliter (ng/ml) PMA and 1 micromolar (uM) A23187 calcium ionophore for 3 hours at 37° C. Then the cells were washed 3 times and cultured in medium for 48 hours to yield a lymphokine-containing supernatant. Preparations obtained from this procedure, PMA/CaI-SN, contained no detectable IFN-G, IL-2, lymphotoxin, or direct cytotoxin, but did contain MPIF. Additionally, all of the studies of PMA/CaI-SN reported herein were performed with substantially pure CTF from the 55 kd peak of a Sephadex G-100sf column chromatography fraction.

G. Cloned Human T Lymphocytes

PBM from normal (healthy, asymptomatic) volunteers were cultured with gamma-irradiated (10,000 rad), allogeneic Daudi lymphoblastoid cells for 48 hours, and then cloned in soft agar in the presence of IL-2. Gregory et al., (1985) *J. Clin. Invest.* 76:2440. Proliferating colonies were isolated and expanded in IL-2-containing liquid culture with frequent, periodic restimulation by irradiated Dudi cells as discussed in Gregory et al., (1985) *J. Clin. Invest.* 76:2440.

To produce lymphokine-containing supernatants from T cell clones, cells that had not been stimulated for 3 weeks or fed IL-2 for 5 days were washed and counted. Then the clones selected for this study were stimulated with irradiated Daudi cells at an optimally determined 4:1 (irradiated Daudi cells to T cells) ratio. The resulting culture medium was sampled at various time points thereafter. Control supernatants were prepared by separately culturing T cell clones and irradiated Daudi cells, and subsequently mixing their supernatant media.

H Molecular Exclusion Chromatography

Lymphokine-containing medium supernatants were concentrated 10-fold by ultrafiltration using Amicon YM-10 membranes (10,000 m.w. cutoff), dialyzed against endotoxin-free PBS (0.01 M phosphate, pH 7.2) and applied to a $2.5 \times 90$ cm column of Sephadex G-100sf equilibrated with endotoxin-free PBS at 4° C. Fractions (4.0 ml) were eluted using PBS at a flow rate of 6 ml/hour. Each fraction was assayed for protein by the Lowry method using bovine serum albumin as a standard. Additionally, samples were assayed for IFN-G using an RIA sensitive to 0.5 U/ml, and for IL-2 by quantitation of thymidine incorporation into the IL-2-dependent murine T cell lines CTLL-4 and HT-2 as described by Gregory et al., (1985) *J. Clin. Invest.* 76:2440. Direct cytotoxin activity was measured by assaying cytotoxicity in the absence of PBM effectors, and measuring $^{51}$Cr release from the target cells in the standard 6 hours assay.

I. Other

All assays were run in triplicate or quadruplicate, and results were calculated as mean plus or minus ($\pm$) one standard deviation. All media and reagents, except where explicitly stated were devoid of detectable endotoxin at the level of 0.01 ng/ml by Limulus amoebocyte lysate assay (E-toxate, Sigma Chem. Co., St. Louis, Mo.). Phenotype determinations were made by indirect immunofluorescence using an ORTHO-MUNE kit available from Ortho Diagnostic Systems, Inc., Raritan, N.J. The supplier's directions were followed in these determinations.

The present invention has been described with respect to preferred embodiments. It will be clear to those skilled in the art that modifications and/or variations of the disclosed subject matter can be made without departing from the scope of the invention set forth herein.

What is claimed is:

1. A substantially pure human proteinaceous lymphokine, which lymphokine:
   (a) has an apparent Mr of about 55 kilodaltons as determined by gel exclusion chromatography, using a gel matrix capable of fractionating proteins of an apparent relative molecular mass of about 6 to about 150 kilodaltons;
   (b) is capable of inducing the secretion of a tumor cell-killing factor that includes tumor necrosis factor-alpha from interferon-gamma-primed monocytes with a cytotoxicity triggering specific activity of at least 50,000 units per milligram protein when said monocytes are primed by culturing in the presence of interferon-gamma for a time period of at least 36 hours;
   (c) is secreted in impure form from differentiated, stimulated normal human helper T cells that express a T3+T4+T8−M1− phenotype; and (d) is substantially free of pyrogen, interferon-gamma, interleukin-2 and direct cytotoxin.

2. The lymphokine of claim 1 wherein said lymphokine has a specific activity of 50,000 to about 300,000 units per milligram protein.

3. A substantially pure human proteinaceous lymphokine having an apparent Mr of about 14 kilodaltons as determined by gel exclusion chromatography, using a gel matrix capable of fractionating proteins of an apparent relative molecular mass of about 6 to about 150 kilodaltons, having a specific activity of at least 50,000 units per milligram protein, that is capable of inducing the secretion of a tumor cell-killing factor that includes tumor necrosis factor-alpha from interferon-gamma-primed monocytes, said lymphokine being substantially free of pyrogen as well as interferon-gamma, interleukin-2 and direct cytotoxin.

4. The lymphokine of claim 3 wherein said lymphokine has a specific activity of 50,000 to about 300,000 units per milligram protein.

5. A method of inducing peripheral blood mononuclear cells to secrete a tumor cell-killing factor that includes tumor necrosis factor-alpha comprising admixing primed effector cells in an aqueous medium with substantially pure CTF present in an amount effective to trigger secretion of a tumor cell-killing factor that includes tumor necrosis factor-alpha, said substantially pure CTF (a) being a human proteinaceous lymphokine having an apparent Mr of about 55 kilodaltons as determined by gel exclusion chromatography, using a gel matrix capable of fractionating proteins of an apparent relative molecular mass of about 6 to about 150 kilodaltons, (b) having a cytotoxicity triggering specific activity of at least 50,000 units per milligram protein, (c) being secreted in impure form from differentiated, stimulated normal human helper T cells that express a T3+T4+T8−M1− phenotype, (d) being capable of inducing the secretion of a tumor cell-killing factor that includes tumor necrosis factor-alpha from monocytes primed in culture for a time period of at least 36 hours with interferon-gamma, and (e) being substantially free of pyrogen as well as interferon-gamma, interleukin-2 and direct cytotoxin.

6. The method according to claim 5 including the further step of recovering said tumor necrosis factor-alpha.

7. The method according to claim 5 wherein said primed effector cells are primed monocytes.

8. The method according to claim 5 wherein said admixing is carried in vitro.

9. The method of claim 5 wherein said substantially pure CTF has a specific activity of 50,000 to about 300,000 units per milligram protein.

10. A method of inducing primed human effector cells to mediate the killing of tumor cells comprising admixing interferon-gamma primed human effector cells in an aqueous medium with an amount of a substantially pure human proteinaceous lymphokine effective to trigger secretion of a tumor cell-killing factor that includes tumor necrosis factor-alpha from said primed cells, and contacting tumor cells to be killed with the secreted tumor-killing factor, said substantially pure lymphokine (a) having an apparent Mr of about 55 kilodaltons as determined by gel exclusion chromatography using a gel matrix capable of fractionating proteins of an apparent relative molecular mass of about 6 to about 150 kilodaltons, (b) having a cytotoxicity triggering specific activity of at least 50,000 units per milligram protein, (c) being substantially free of pyrogen as well as interferon-gamma, interleukin-2 and direct cytotoxin, (d) present in impure form in a secretion from differentiated, stimulated normal human helper T cells that express a T3+T4+T8−M1− phenotype, and (e) capable of inducing secretion of a tumor cell-killing factor that includes tumor necrosis factor-alpha from monocytes primed in culture for a time period of at least 36 hours with interferon-gamma.

11. The method according to claim 10 wherein said lymphokine is substantially unglycosylated.

12. The method according to claim 10 wherein said effector cells are primed monocytes.

13. The method according to claim 10 wherein said primed effector cells are primed macrophages and are triggered in vivo in a tumor in a patient and the tumor cells contacted with the tumor-killing factor containing tumor necrosis factor-alpha are the cells of said tumor within which said primed monocytes are triggered.

14. The method according to claim 13 wherein the effective triggering amount of said lymphokine is about 1 to about 100 units per milliliter of plasma of said patient.

15. The method according to claim 13 wherein the effective triggering amount of said lymphokine is about 60 to about 60,000 units per kilogram of body weight of said patient.

16. The method according to claim 13 including the additional steps of
   (a) providing the patient with in vitro primed monocytes in addition to the primed effector cells present in said tumor; and
   (b) maintaining the patient for a time period sufficient for the additional primed monocytes to concentrate in the tumor;
   said steps (a) and (b) being carried out prior to said admixing step.

17. The method according to claim 16 wherein said primed monocytes are provided by
   (i) obtaining a monocyte-containing leukocyte preparation from said patient or a compatible human donor;
   (ii) admixing said preparation in vitro with a priming amount of interferon-gamma; and
   (iii) maintaining the leukocyte and interferon-gamma admixture so formed for a time period sufficient for said monocytes to be primed.

18. The method according to claim 10 wherein said primed effector cells are triggered in vitro and the tumor cells contacted with the tumor cell-killing factor are supplied exogenously within about 10 hours of said triggering.

19. The method according to claim 18 wherein the effective triggering amount of said lymphokine is about 3 to about 300 units per milliliter for about $5 \times 10^5$ peripheral blood mononuclear cells as said effector cells, and said peripheral blood mononuclear cells are primed for a time period of 48 hours using 150 units per milliliter of interferon-gamma using a peripheral blood mononuclear cell to target tumor cell ratio of 50:1 and $10^4$ Act D-treated WEHI 164 cells as tumor cells.

20. The method of claim 10 wherein said lymphokine has a specific activity of 50,000 to about 300,000 units per milligram protein.

* * * * *

UNITED STATES PATENT AND TRADEMARK OFFICE
CERTIFICATE OF CORRECTION

PATENT NO. : 4,785,077
DATED : November 15, 1988
INVENTOR(S) : Kornbluth et al.

It is certified that error appears in the above-identified patent and that said Letters Patent is hereby corrected as shown below:

Column 1, after the title "DESCRIPTION" and before the heading "1. Technical Field", insert the following paragraph:

--This invention was made with government support under Contract No. CA 28166 awarded by the National Institutes of Health. The government has certain rights in the invention.--

Signed and Sealed this

First Day of February, 1994

*Attest:*

BRUCE LEHMAN

*Attesting Officer*  *Commissioner of Patents and Trademarks*